(12) United States Patent
Fingler et al.

(10) Patent No.: US 7,995,814 B2
(45) Date of Patent: Aug. 9, 2011

(54) DYNAMIC MOTION CONTRAST AND TRANSVERSE FLOW ESTIMATION USING OPTICAL COHERENCE TOMOGRAPHY

(75) Inventors: Jeffrey P. Fingler, Pasadena, CA (US); Scott E. Fraser, La Canada, CA (US); Daniel Schwartz, San Francisco, CA (US)

(73) Assignees: California Institute of Technology, Pasadena, CA (US); The Regents of the University of California, Oakland, CA (US)

( * ) Notice: Subject to any disclaimer, the term of this patent is extended or adjusted under 35 U.S.C. 154(b) by 1082 days.

(21) Appl. No.: 11/767,187

(22) Filed: Jun. 22, 2007

(65) Prior Publication Data
US 2008/0025570 A1 Jan. 31, 2008

Related U.S. Application Data

(60) Provisional application No. 60/816,431, filed on Jun. 26, 2006, provisional application No. 60/853,684, filed on Oct. 23, 2006.

(51) Int. Cl.
*G06K 9/00* (2006.01)
*A61B 6/00* (2006.01)
(52) U.S. Cl. .......................... 382/128; 378/4
(58) Field of Classification Search ................. 382/128, 382/129, 130, 131, 132, 133, 134, 107; 356/432, 356/479, 497; 378/4, 21–27, 101, 901; 128/920, 128/922
See application file for complete search history.

(56) References Cited

U.S. PATENT DOCUMENTS

| 7,075,658 | B2 * | 7/2006 | Izatt et al. ............. 356/479 |
| 7,330,273 | B2 * | 2/2008 | Podoleanu et al. ..... 356/497 |
| 7,359,062 | B2 * | 4/2008 | Chen et al. ............. 356/479 |
| 2005/0171438 | A1 | 8/2005 | Chen et al. |

OTHER PUBLICATIONS

Park et al., Real-Time Fiber-Based Multi-Functional Spectral Domain Optical Coherence Tomography at 1.3µm, Optics Express, (2005) pp. 3931-3944, vol. 13, No. 11.

* cited by examiner

*Primary Examiner* — Abolfazl Tabatabai
(74) *Attorney, Agent, or Firm* — Seth D. Levy; Davis Wright Tremaine LLP

(57) ABSTRACT

The methods described herein are methods to ascertain motion contrast within optical coherence tomography data based upon phase variance. The phase variance contrast observes the nanometer scale motion of scatterers associated with Brownian motion and other non-flow motion. The inventive method of calculating motion contrast from the phase variance can differentiate regions of different mobility based on the motion contrast differences, and can use the phase information to characterize mobility properties of the scatterers. In flow regions, the inventive method for acquiring and analyzing motion contrast can identify the regions as well as characterize the motion. Furthermore, the inventive method can determine quantitative flow estimation, the index of refraction variations, and absorption variations within flow regions.

20 Claims, 37 Drawing Sheets

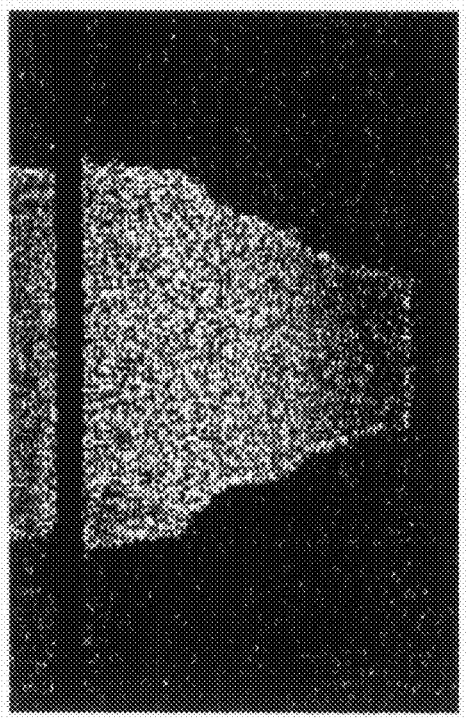
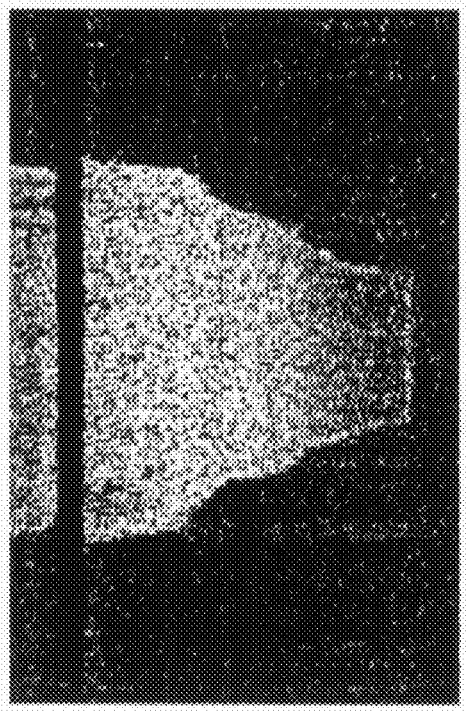

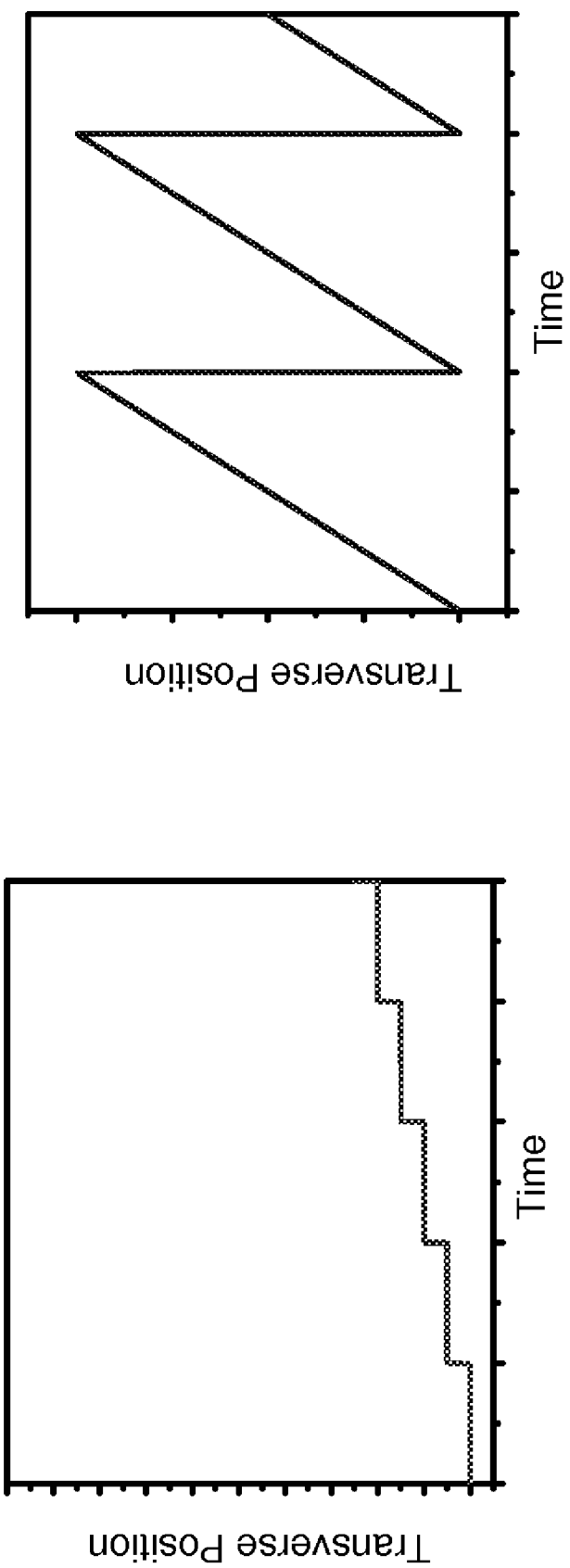

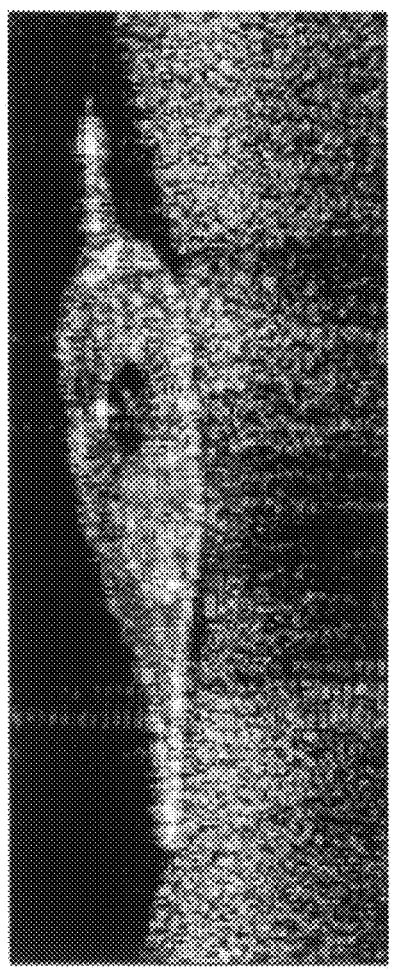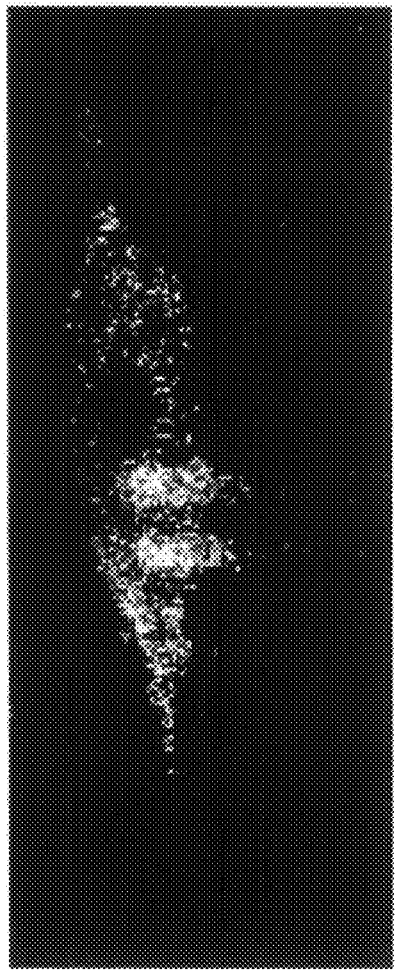
Fig. 13A
Fig. 13B

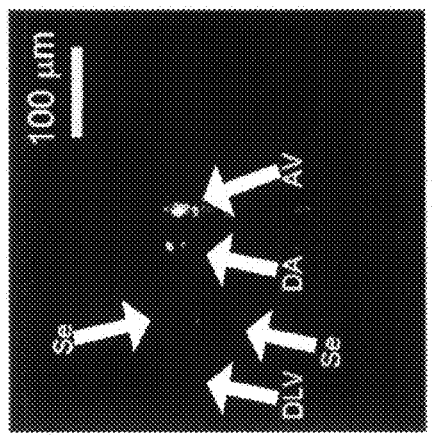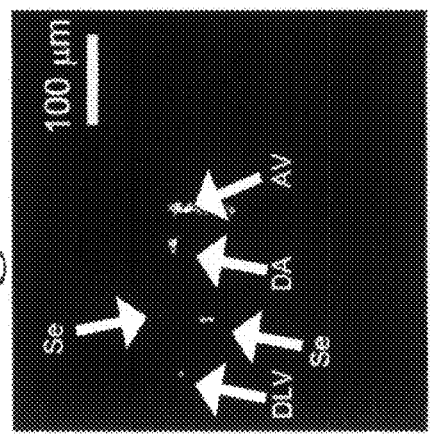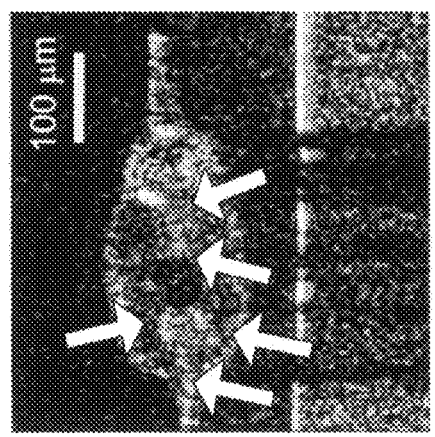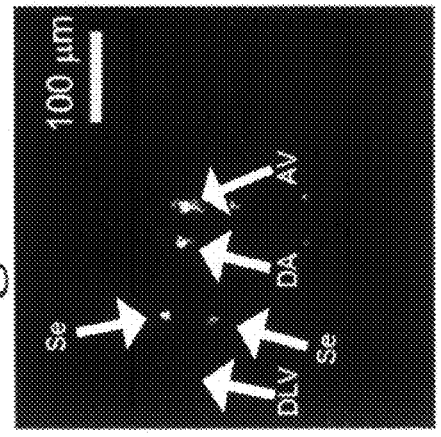

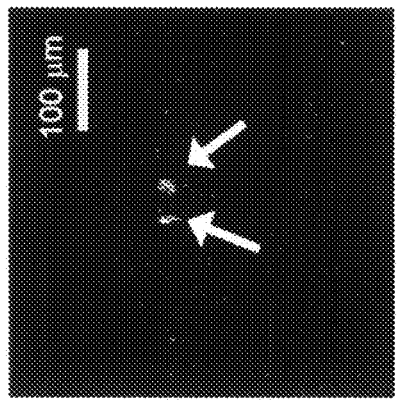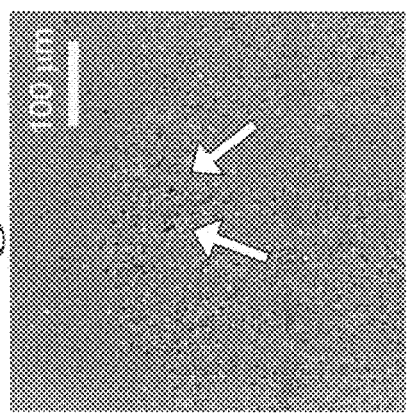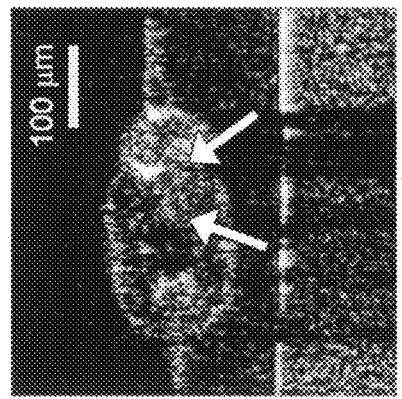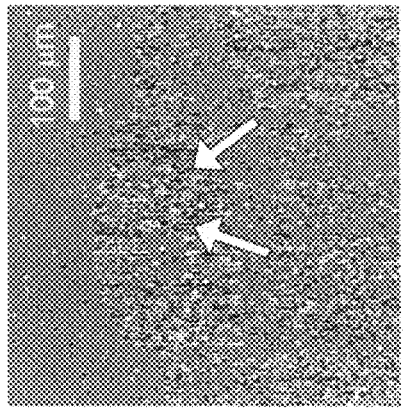

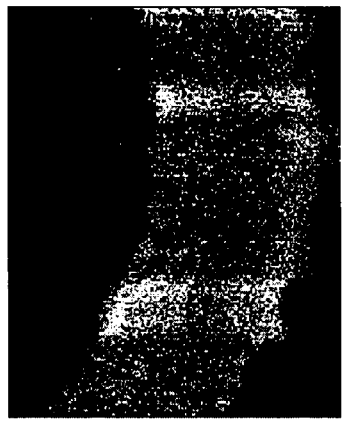
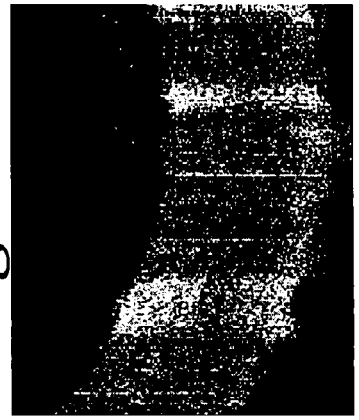
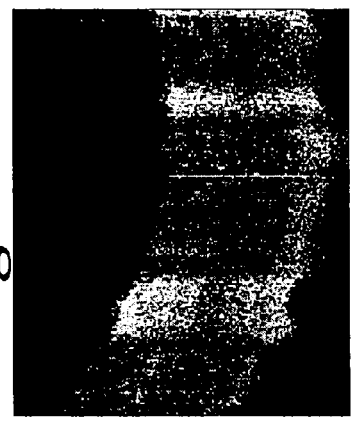

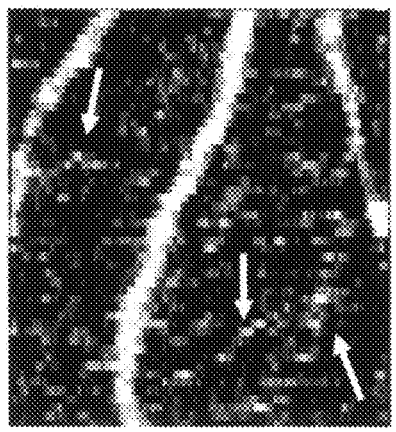
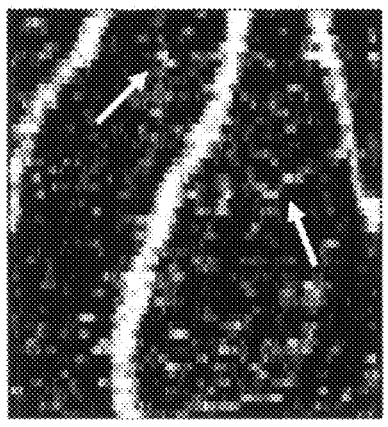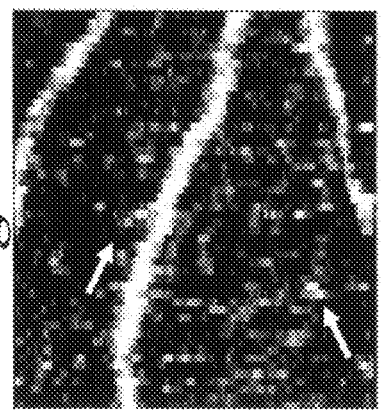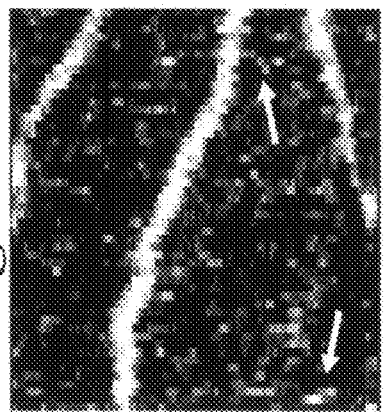

DYNAMIC MOTION CONTRAST AND TRANSVERSE FLOW ESTIMATION USING OPTICAL COHERENCE TOMOGRAPHY

CROSS-REFERENCE TO RELATED APPLICATIONS

This application claims the benefit under 35 U.S.C. §119(e) of U.S. Provisional Application Nos. 60/816,431, filed on Jun. 26, 2006, and 60/853,684, filed on Oct. 23, 2006, each of which is incorporated herein by reference.

FIELD OF THE INVENTION

Optical coherence tomography (OCT) is an optical imaging technique that allows for three dimensional visualization and analysis of structures in a variety of biological systems that are difficult to examine and analyze with other imaging techniques. The embodiments of this invention describe methods to produce motion contrast for a variety of motion types in an OCT system by acquiring and analyzing data according to the inventive method based on phase variance and/or intensity fluctuation analysis.

BACKGROUND OF THE INVENTION

OCT is a non-invasive optical imaging technique which produces depth-resolved reflectance imaging of samples through the use of a low coherence interferometer system. OCT imaging allows for three-dimensional visualization of structures in a variety of biological systems not easily accessible through other imaging techniques, including but not limited to the retina of the eye.

Vascular visualization and quantitative information of blood flow is very important for the diagnosis and treatment of many diseases. In OCT imaging, a type of phase sensitive analysis called Doppler OCT is the primary form of vascular visualization and diagnostic. Phase is a type of high resolution position measurement of a reflection along the optical path length of the imaging system, which is cyclic of the frequency of half the wavelength of the imaging light. A depth position change of half the imaging wavelength will produce the same phase measurement. Changes in phase are proportional to the axial flow, the flow component parallel to the imaging direction designated by $v(\cos \theta)$, where v is the velocity of the flow and $\theta$ is the angle between the flow direction and the imaging light. Phase noise in the system based on the local signal to noise ratio determines the minimum axial flow measurement, which limits the visualization of flow in cases where v or $\cos \theta$ is very small. For cases such as in the retina, a lot of flow is nearly perpendicular to the imaging direction such that $\theta \sim 90°$ and $\cos \theta \sim 0$. In these cases, the velocity v of the flow must be extremely high to be able to visualize the flow with this method.

The progress of development in OCT is towards faster imaging technologies and techniques in order to image larger regions in the same amount of time. In order to maintain fast imaging speeds, Doppler OCT imaging techniques only use a few successive depth reflectivity measurements called A-scans (the typical number is around 5), and average the phase change between each of them. The limited statistics and the short time between the A-scans (and also the phase measurements) severely limit the minimum observable axial flow, allowing for only visualization of the fastest flows.

Demonstrated variance calculations of the phase changes for this situation do not add additional motion contrast to the images. This lack of additional contrast is because the phase error due to the local signal to noise ratio dominates the calculations in all regions except in the same fast flow regions visualized with the Doppler OCT technique.

Speckle analysis looks at intensity variations of images, which has limited work demonstrated in the field of OCT. Most of the work with speckle in OCT has been directed towards the reduction of speckle artifacts from multiple reflections within the sample to improve image quality. Demonstrated speckle analysis techniques utilize spatial variations of intensity from a single static image to characterize regions and identify regions of flow. These techniques are only capable of analyzing regions much larger than the spatial resolution of the imaging system and have typically been used in non-OCT imaging situations which do not have the depth discrimination capabilities of OCT.

Accordingly, there is a need in the field of OCT for an accurate and efficient method to ascertain flow of biological fluids to assist in the diagnosis and treatment of many diseases. In particular, there is a need to develop a method capable of estimating transverse flow velocity and to ascertain motion contrast with OCT systems.

SUMMARY OF THE INVENTION

This application describes the acquisition and analysis methods to produce motion contrast based on phase variance and intensity fluctuation and/or speckle information in an OCT system for a variety of motion types. The phase variance contrast utilizes the temporal evolution of the measured phase variance of the motion to identify and characterize mobile scatterers within the OCT sample images. Acquisition methods are presented which demonstrate a highly efficient acquisition capable of screening for regions of mobility as well as an acquisition capable of quantitative diagnostics of the scatterers.

In another embodiment, the method further comprises using the temporal fluctuations in intensity of the OCT images. The temporal fluctuations in intensity of the OCT images can also be used as another form of contrast to observe the fluctuations associated with flow and absorption changes within the depths of the sample.

The methods and techniques developed herein demonstrate motion contrast within optical coherence tomography images. The motion contrast, and in particular the phase variance contrast is able to observe the nanometer scale motion of scatterers associated with Brownian motion and other non-flow motion. The contrast calculated from the phase variance can differentiate regions of different mobility based on the differences in motion contrast and can use the phase information to characterize mobility properties of the scatterers. For flow regions, the analytical methods described can identify the regions as well as characterize the motion. Quantitative flow estimation can be determined for flow, independent of the orientation relative to the imaging direction. The shadowing of contrast in the phase variance and the intensity fluctuation calculations can be used to determine the index of refraction variations as well as absorption variations within flow regions.

The acquisition methods described herein demonstrate a low efficiency, highly informative diagnostic acquisition as well as an efficient, three-dimensional screening acquisition. The highly efficient acquisition allows for three-dimensional visualization of mobile regions such as a vascular region within the sample. The flexibility of these inventive methods allow for the identification of regions of intermittent flow, such as identification of blood cell motion in the microvasculature. The ability to identify regions of intermittent blood flow can assist in the diagnosis and treatment of a patient in need thereof.

A computer readable medium having computer executable instructions for ascertaining motion contrast in a sample is also contemplated herein. The computer readable medium having computer executable instructions for ascertaining motion contrast comprises acquiring data using an OCT system by performing one or more scan of the sample, ascertaining phase variance of the data, and ascertaining motion contrast in the sample based upon the phase variance. The computer readable medium having computer executable instructions for ascertaining motion contrast may further utilize intensity fluctuation and/or speckle information for ascertaining motion contrast in a sample. The phase variance contrast may utilize the temporal evolution of the measured phase variance of the motion to identify and characterize mobile scatterers within the OCT sample images. The computer readable medium having computer executable instructions for ascertaining motion contrast may also include acquisition methods capable of screening for regions of mobility and quantitative diagnostics of the scatterers.

An OCT machine comprising computer readable media having computer executable instructions for ascertaining motion contrast in a sample is also contemplated herein. The computer readable medium having computer executable instructions for ascertaining motion contrast on the OCT machine comprises acquiring data using the OCT system by performing one or more scan of the sample, ascertaining phase variance of the data, and ascertaining motion contrast in the sample based upon the phase variance. The OCT machine comprising computer readable media having computer executable instructions for ascertaining motion contrast may further utilize intensity fluctuation and/or speckle information for ascertaining motion contrast in a sample. The phase variance contrast may utilize the temporal evolution of the measured phase variance of the motion to identify and characterize mobile scatterers within the OCT sample images. The OCT machine comprising computer readable media having computer executable instructions for ascertaining motion contrast may also include acquisition methods capable of screening for regions of mobility and quantitative diagnostics of the scatterers.

DETAILED DESCRIPTION OF THE INVENTION

The OCT system used for the data presented herein is a spectral domain optical coherence tomography (SDOCT) setup as shown in FIG. 1, with a fiber-optic interferometer used to split the light between a reference arm and a sample arm. The acquisition and analysis techniques described herein do not depend on the type of OCT system used, only on the number of intensity and phase samples taken as well as the speed of each depth reflectivity measurement, called an A-scan.

The phase change $\Delta\phi(z_i,T)$ measured for a given depth $z_i$ for a time separation T is a combination of several factors effecting the measurement:

$$\Delta\phi(z_i,T)=\Delta\phi_{motion,scatterer}(z_i,T)+\Delta\phi_{motion,bulk}(T)+\Delta\phi_{error,SNR}(z_i)+\Delta\phi_{error,other}(z_i)$$

The phase change $\Delta\phi(z_i,T)$ contains not only the individual motion of the scatterer at the depth $z_i$ which is designated by $\Delta\phi_{motion,scatterer}(z_i,T)$ (which is the motion of interest), but it also contains the bulk relative motion between the sample and the system along the imaging (axial) direction $\Delta\phi_{motion,bulk}(T)$. $\Delta\phi_{error,SNR}(z_i)$ is the phase error associated with the SNR of the data calculated at the depth $z_i$. Published experimental results have calculated that the accuracy of measured phase changes is determined by the local signal to noise ratio and is of the form:

$$\sigma_{\Delta\phi,SNR\_error}(z)=1/\sqrt{SNR(z)}$$

$\Delta\phi_{error,other}(z_i)$ encompasses the other phase errors which may occur for OCT phase measurements, including but not limited to transverse scanning errors, transverse motion of the sample, or artifacts associated with limited depth sampling during axial motion of the sample. To be able to identify the motion of the scatterers for a given depth $\Delta\phi_{motion,scatterer}(z_i,T)$, the effects of the other forms of phase noise need to be removed or reduced. Each phase measurement calculated the relative motion between a depth reflection of the sample and the rest of the imaging system. From a single phase change measurement, it is not possible to separate the bulk relative axial motion between the sample and system from the individual motion of a mobile region within the sample. Without the ability to remove this bulk motion, the minimum measurable motion within the sample is limited by the bulk system and sample motion.

One of the methods of determining the bulk sample motion is using an additional motion measurement, like an interferometer for example, to determine the motion of the strongest reflection within the sample. With Fourier domain optical coherence tomography systems, which includes spectral domain optical coherence tomography and swept source optical coherence tomography (also referred to as optical frequency domain imaging), all of the depths of the sample are measured at the same time. With the phase change information available for all of the depth reflections, it is possible to extract the bulk motion for removal.

In some scenarios, there is a strong reflector within the sample that can be used as a stationary reflection to be used as a reference for the bulk phase removal. Many cases do not contain a highly reflective stationary reflector to use, so the entire sample depth must be used to calculate the bulk motion. There are several ways to analyze the phase change information from all of the depths to calculate the bulk sample motion. With the large phase noise associated with depths with no reflectance or signal near the noise level, the mean calculated from all of the phase changes can be distorted due to these low signal terms. Thresholding of the phase data analyzed can reduce the effect of these terms. The mode of the calculated phase changes can be used to determine the bulk motion as well, with an accuracy determined by the parameters used in the mode calculation.

A weighted mean calculation allows for the estimation of the bulk motion for a variety of sample cases. The bulk motion in this method is calculated by $\Delta\phi_{motion,bulk}(T)=\Sigma[w(z_i)\Delta\phi(z_i,T)]/\Sigma[w(z_i)]$, where the weighting factor $w(z_i)$ is dependant on the type of imaging situation. The weighting factor can be determined by the linear OCT intensity $I^2(z_i)$, which relies on the highest reflections within the sample being stationary. Using the weighting factor of the OCT amplitude $I(z_i)$, the calculation is more sensitive to the phase noise of the low signal terms within the measurement. By incorporating a threshold term into the weighting factor, the phase noise effect from the low signal terms can be reduced in all cases. The weighting term can also contain a spatial dependence to deal with specific sample and motion properties. For example, the stationary regions of a sample below a high velocity flow region can appear non-stationary with the phase change measurements which can require a different weighting above and below the flow regions within the sample. The weighting factor can also incorporate weighting based on the shape of the local intensity function of the depth reflectivity measurement. Artifacts created by phase motion calculations of the side lobes and dips of reflectance profiles can cause unwanted discrepancies which can distort the bulk motion estimation.

With the cyclic nature of the phase measurements, phase changes are forced to be limited between $-\pi$ and $+\pi$. Motions larger than this amount (equivalent to a quarter of the wavelength of the imaging light) suffer from phase wrapping and are miscalculated (a phase change of $+\pi+\delta$ is misinterpreted as $-\pi+\delta$). In phase measurement cases where the bulk motion of the sample is approximately $+/-\pi$, the phase error will cause the calculated phase change distribution to appear similar to the data presented in FIG. 2. Without additional correction to the phase change distribution, the calculated bulk motion will be inaccurate. Before bulk motion calculations occur as described above, the distribution of phase should be re-centered such that the mean more accurately represents the motion.

After the removal of the estimated bulk motion from the calculated phase changes $\Delta\phi(z_i,T)-\Delta\phi_{motion,bulk}(T)$, the variance of this quantity can be approximated by the sum of the variance of the individual components composing the phase change:

$$\sigma_{\Delta\phi}^2(z_i,T)=\sigma_{\Delta\phi,motion\_scatterer}^2(z_i,T)+\sigma_{\Delta\phi,SNR\_error}^2(z_i)+\sigma_{error\_other}^2(z_i)$$

The motion of interest as the source of contrast for the phase variance analysis is the scatterer motion phase variance term $\sigma_{\Delta\phi,motion\_scatterer}^2(z_i,T)$. The SNR-limited phase error $\sigma_{SNR\_error}^2(z_i)$ is determined by the local signal to noise ratio as described earlier and is independent of the time separation of the phase measurement T. The last term of the calculated phase variance $\sigma_{error\_other}^2(z_i)$ incorporates all of the other phase error factors which include the contributions from the error created from the bulk motion calculation method as well as all of the other effects described for $\Delta\phi_{error,other}(z_i)$. The SNR-limited phase error is generally the limiting factor to visualizing the motion of the scatterers.

There are several types of motion which contain components that are observable through the motion scatterer variance measurement of the phase motion which include, but are not limited to:

Variations in the axial component of flow
Transverse flow effects of uncorrelated scatterers
Axial component of Brownian-type random motion
Ensemble statistical effects of uncorrelated scatterers (multiple scatterers located within the imaging resolution of the system and identified as a single scatterer location)

Each of the above mentioned types of motion have a variance of motion which increases with the time separation between position (phase) measurements. In most cases, the SNR-limited phase error associated with each measured reflection is the limiting factor to the minimum scatterer motion that can be observed. Since this phase error is independent of time, waiting longer between phase measurements allows for the variance of the scatterer motion to increase beyond the limits of the phase error. Further increases to the time separation used for the phase changes will continue to increase the measured phase change variance. This will continue until the calculated phase variance reaches a level comparable to a completely random phase signal. Further increases to the motion of the scatterers should not increase the measured phase variance beyond the completely random phase.

One of the effects that occurs with even longer time separations associated with transverse flow is an appearance of motion shadowing below the regions of flow. This is due to the index of refraction changes which occur within regions of transverse flow. The phase measurement in OCT is not simply a change in the position of a given reflector; it is the change in the optical path length to that same reflector. Therefore, a phase change also measures all of the refractive index variations which have occurred during the time separation T over the entire depth until the measured reflection.

$$\Delta\phi(z,T)=\frac{4\pi}{\lambda_0}\left(\int_0^z \Delta n(z',T)\,dz'+n(z)\Delta z\right)$$

For a stationary reflector measured below a region of average refractive index change $\Delta\bar{n}(z',T)$ which extends a depth of $z_n$, the calculated phase change is:

$$\Delta\phi(z,T)=\frac{4\pi}{\lambda_0}\Delta\bar{n}(T)z_n$$

For example, to create a completely random phase measurement measured below flow of a vessel of thickness 15 μm, the required minimum average refractive index variation in the case of an imaging wavelength of approximately 800 nm:

$$\frac{\Delta\bar{n}_{rms}(T)}{\bar{n}}\approx 0.006=0.6\%$$

With the knowledge of the time separation of the onset of refractive index shadowing within the phase contrast images and knowledge of the refractive indices of the constituents within the flow region, characteristics of the transverse flow and the density variations of the flow can be determined. Accordingly, estimating refractive index variations within flow regions assists in ascertaining motion contrast in an optical coherence tomography system.

To demonstrate the increase of measured variance motion with increased time separation between phase measurements, the case of Brownian motion is shown. 2% agarose wells are created and filled with an Intralipid solution diluted to match the scattering intensity of the agarose. The agarose is a gelatin which is expected to be stationary in comparison to the mobile Intralipid scatterers.

The phase variance is calculated for this image region for different time separations of the phase change. The images presented in FIGS. 5, 6, and 7 demonstrate a successive increase in the time separation, starting from the shortest time capable with the experimental imaging system. The shortest time separation phase variance images are dominated by the SNR-limited phase noise of the image. As the time separation increases, the phase variance calculation of the region containing the mobile Intralipid solution increased as well.

In order to properly image the contrast created by the scatterer motion, the SNR-limited phase noise should be removed. One of the methods to remove it is to use phase variance calculations from different time separations $T_1$ and $T_2$. If we can assume the phase error from other sources is negligible, the calculated phase variance for these time separations is of the form:

$$\sigma^2_{\Delta\phi}(z_i,T_1)\cong\sigma^2_{\Delta\phi,scatterer}(z_i,T_1)+\sigma^2_{\Delta\phi,SNR}(z_i)$$

$$\sigma^2_{\Delta\phi}(z_i,T_2)\cong\sigma^2_{\Delta\phi,scatterer}(z_i,T_2)+\sigma^2_{\Delta\phi,SNR}(z_i)$$

By choosing the parameters $T_2=\beta T_1$ where $\beta \gg 1$, it is assumed that for the motion of the scatterers within the system $\sigma^2_{\Delta\phi,scatterer}(z,T_2) \gg \sigma^2_{\Delta\phi,scatterer}(z,T_1)$. The basic phase contrast metric used to create the phase variance contrast image in this case is chosen to be $\sigma^2_{\Delta\phi}(z,T_2) - \sigma^2_{\Delta\phi}(z,T_1)$ such that:

$$\sigma^2_{\Delta\phi}(z,T_2) - \sigma^2_{\Delta\phi}(z,T_1) \approx \sigma^2_{\Delta\phi,scatterer}(z,T_2)$$

With the form known for the SNR-limited phase noise, numerical estimates of the expected values can be used to eliminate them from the phase variance images. Numerical estimates of the phase noise are based on the OCT intensity signal of the reflection and the noise properties of the imaging system as described earlier. This case demonstrates similar contrast images based on the accuracy of the noise estimation.

Looking at the time evolution of the phase variance change can allow for the characterization of the mobility of the scatterers. FIG. 10 demonstrates data acquired from phase variance calculations for different time separations of the Brownian motion of several different sized microspheres in water, a single scatterer in water with diameters ranging from 0.5 μm to 5 μm. Phase variance data is a way to visualize the random motions due to thermal fluctuations. The expected average motion of these scatterers over time equals zero, requiring the variance calculation to image the motion. The 0.5 μm and 5 μm diameter cases shown are for cases with high OCT intensity signal, so the phase error for these phase measurements were negligible relative to the scatterer motion. The case of the 2 μm diameter sphere was chosen for its low OCT signal, where the phase errors in variance measurements were not negligible. While the expected form of the motion should follow parallel with the other cases, the phase error combines with the motion to produce the form shown in FIG. 10. With enough data measuring phase variance data against time separation of phase changes, the motion data can be extracted from the combined phase variance data.

For the phase variance data measured of the Brownian motion (the data which is less than the random phase variance saturation), the calculated motion is the combination of the time insensitive phase error and the Brownian motion which is of the form:

$$\sigma^2_{\Delta\phi}(z_i,T) = A^2 + DT^\gamma$$

By fitting the phase variance data over time to the expected form of the motion, the characteristic motion parameter D (the diffusion constant) of the scatterers can be determined.

Data Acquisition Methods

In order to acquire the data required to identify and/or characterize regions of mobility, phase information from large time separations is required. One of the simplest acquisition methods is to wait at each transverse location, acquiring phase information over time, waiting long enough to acquire the required statistics and the temporal information of the phase change evolution. In terms of OCT scan terminology, an A-scan is the term for a single depth reflectivity measurement. Multiple A-scans acquired at the same transverse location over time is referred to as an M-scan. Multiple A-scans acquired over a range of transverse locations is referred to as a B-scan. The process of waiting at each transverse location creating M-scans, and repeating this over a range of transverse location will be called a MB-scan for this application.

The MB-scan is the easiest way to acquire the statistics and temporal evolution information of the phase variance in order to characterize the mobility of the scatterers. This characterization includes quantification of the flow within regions, along the imaging direction as well as transverse to it (described later). Other characterization capabilities with this information include factors such as the diffusion constant, the scatterer density, and statistical flow information. The only limitation to this method is the inefficiency of the acquisition. The time required to visualize a three-dimensional spatial region with the temporal information of this method would be too long for some applications. A faster acquisition method capable of some of the phase variance contrast visualization is required for screening large three-dimensional regions. Instead of waiting at one location over time until the motion is large enough to produce motion variance contrast, data can be acquired across multiple locations before coming back to the original locations to get additional phase information. This acquisition method is described by acquiring multiple B-scans over time for the same transverse region, which will be called a BM-scan for this application.

The BM-scan is a very efficient method of acquiring phase information with a large time separation without sacrificing total acquisition time of the image. There is limited temporal information with this acquisition method, but the phase information which is acquired allows visualization of slow motions not visible with analysis from successive A-scan acquisitions. Quantitative flow analysis with this method is limited in comparison to the MB-scan. A schematic of some examples of these acquisition methods is shown in FIG. 11.

Images created using one form of the MB-scan and the BM-scan over the tail of a zebrafish are demonstrated in FIGS. 12 and 13. While the phase variance contrast images in both figures identify the same regions of mobility, the BM-scan produces contrast more than 4 times stronger than the MB-scan. This is not unexpected considering that the BM-scan uses phase changes for time separations 40 times larger than used for the presented MB-scan. The contrast image for the BM-scan demonstrates shadowing of the phase variance contrast image due to the index variations of the flow regions associated with the large time separations.

The cases demonstrated in FIGS. 12 and 13 compare the same region of the sample. The BM-scan demonstrated above contains approximately 2.5 times more transverse pixels in a total imaging time reduced by a factor of 3 compared to the above MB-scan. BM-scan acquisition times can be reduced further by the adjustment of the number of transverse locations, adjustment of the statistics used to calculate the phase change variance, reduction of the A-scan acquisition time of the system and by improving the transverse scanning capabilities of the system.

Transverse Flow Estimation Methods

Park et al. [1] published results for the expected phase error to occur while transverse scanning over uncorrelated sample reflections as a function of the fraction of the beam diameter scanned between successive phase measurements. According to the Park definition, standard deviation of the phase difference is equivalent to the square root of what is termed phase variance herein.

In order to create phase contrast in the shortest amount of acquisition time, the analysis performed in Park was to determine the limitations of phase contrast between successive A-scans while scanning transversely and creating a B-scan. What was not mentioned was the possibility of using this expected phase error for relative transverse motion between the sample illumination and the sample reflections as a quantitative measure of transverse flow.

If several A-scans are performed at the same transverse position separated by a time T, there will be a phase noise term which appears due to relative transverse motion between the sample illumination and the sample reflections. With the illumination at the same transverse position at successive measurements, the noise term comes from transverse flow, particularly from uncorrelated reflections such as those found in blood. Consider the case of a Gaussian illumination beam with a $1/e^2$ beam width=d at the focus, and using phase measurements taken at the same transverse position in the same separated by T. The variance of the phase changes is determined for a transverse motion of the scatterer $\Delta x$ between the phase measurements, created by a transverse velocity $v_x$ during the time separation T. Defining the fraction of the beam width as $\Delta x/d$, the variance of the phase error due to the transverse motion is calculated to be:

$$\sigma_{\Delta\phi}^2 = \frac{4\pi}{3}\left(1 - \exp\left(-2\left(\frac{\Delta x}{d}\right)^2\right)\right) = \frac{4\pi}{3}\left(1 - \exp\left(-2\left(\frac{v_x T}{d}\right)^2\right)\right)$$

Due to the other error terms which occur in the phase measurements, the accuracy of this technique may be limited to the accuracy of the calibrations of the system and the removal of other phase error terms. From the data presented in Park, the dynamic range of quantitative measure of transverse flow with this analysis appears to be limited to motion which is approximately $20\% \leq \Delta x/d \leq 80\%$ in the time period T. SNR-limited phase noise limit the minimum transverse velocity which can be determined with this method. The upper limit was approximated by the saturation limit of a random phase noise signal limited to be between $-\pi$ and $\pi$. This equation only allows for qualitative measures of flow such that $v_x T/d > \sim 0.8$. Increased temporal information can improve the dynamic range of this transverse flow measurement.

In the example of retinal imaging, with a time separation of 40 ms and a focused beam diameter of 20 μm, the dynamic range of quantitative transverse flow calculations is approximately 0.1 mm/s to 0.4 mm/s.

Altering the dynamic range of quantitative flow can be achieved by changing the transverse resolution of the imaging system, or by altering the time separation of measurements T. For example, if retinal imaging was changed to have a time separation of 10 ms with a 30 μm beam diameter, the dynamic range of quantitative transverse flow calculations is approximately 0.6 mm/s to 2.4 mm/s. If the statistics for the phase measurement in this case was sufficient, the phase data acquired with 10 ms time separation can be used to calculate phase variance for a time separation of 20 ms as well (every second phase position measured). This would increase the dynamic range of the quantitative flow measurement by a factor of 2, which in this case results in approximately 0.3 mm/s to 2.4 mm/s.

A second method of determining transverse flow uses the fact that the refractive index variations of transverse flow regions create shadowing artifacts below the flow within the image. If the time separation for the onset can be identified, the depth extent of the flow region can be identified, and the average index of refraction change within the region can be identified. With knowledge of the refractive indices of the scatterers within the flow region, transverse flow rates can be identified. This method is likely to be useful for cases where the flow regions contain multiple types of constituents, like plasma and blood cells within blood vessel flow.

Another method of quantitatively determining transverse flow uses a combination of BM-scans and MB-scans over a region of the sample. The BM-scan phase variance contrast is a highly efficient method of identifying three-dimensional regions of mobility within a sample. With the BM-scans, three-dimensional vasculature can be identified and the directionality of the flow relative to the imaging direction can be used. The MB-scan can be used over the identified vessel of interest and selectively analyzing that specific regional flow. The average axial flow determined from the average phase change can determine the flow within the region. With the location identified by the screening method and the increased statistics available from the MB-scan, small axial flow components can be calculated. With the directionality of the vessel known, the flow within the vessel can be geometrically calculated. The temporal evolution of the phase variance can provide additional correlation to the flow calculation through an estimation of the transverse component of the flow.

Transverse Motion Noise Removal

One of the issues associated with the acquisition methods is the additional noise which accompanies the increased time separation. While the scatterer motion is given more time to move between phase measurements, the sample is also given more time to move as well. The axial motion of the sample is removed through bulk motion removal methods described earlier. The bulk transverse motion is not compensated for with the previous method. As derived in literature, relative transverse motion between the sample and the imaging beam creates a phase error depending on the magnitude of fraction of the imaging beam waist which has been moved [1]. The derivation of the phase noise is based upon the assumption of uncorrelated scatterers within the sample, which is not the case for all reflections within layers samples like the retina.

FIG. 14 demonstrates OCT images taken of a slice through a mouse retina, with the averaged OCT intensity image compared against the phase variance contrast image. This contrast image used numerical estimates to remove the SNR-limited phase noise as well as applying median filtering to further reduce artifacts. The regions of motion in the contrast image are clearly observed, including the top retinal vessels with contrast shadowing occurring below the vessels and the bottom choroidal vessels which do not have any OCT signal below to produce additional shadowing. In this contrast image, there is a minimal amount of bulk transverse motion occurring in the sample. That is not the case for the phase variance contrast image in FIG. 15, which is taken at the same transverse locations within the retina but at a later time when larger transverse motion is occurring. Within this image, visualization of the flow regions is still possible but there is a significant amount of additional noise which hinders visualization.

The approach used to deal with the bulk transverse motion is to assume that the entire contrast image contains the same level of additional phase noise at all transverse locations for the case of the BM-scan. Since the BM-scan acquires data at all transverse locations in a short time frame, all of these points should be experiencing the same motion and the same resulting phase noise. Using all of the contrast data points which are not zero after SNR phase noise removal, the statistics of the contrast image data can be used to try and remove the effect of the transverse motion. For the mean and standard deviation of the non-zero contrast data of the image of $\mu$ and $\sigma$, respectively, the contrast image $C(x,z)$ can be adjusted through many methods including a removal and normalization of the form:

$$(C(x, z) - (\mu + \alpha\sigma))\left(\frac{3.3}{3.3 - (\mu + \alpha\sigma)}\right) = C'(x, z)$$

In this case, 3.3 radians$^2$ is the amount chosen as the phase variance contrast value as the expected maximum value associated with a random phase measurement. The parameter $\alpha$ is chosen to be adjustable to improve the visualization of regions which may be removed by over-estimation of the phase noise. FIG. 16 demonstrates the above mentioned additional phase removal for the case of $\alpha=0$.

FIG. 17 demonstrates the noise removal process when applied to the retinal contrast images acquired over time. Each two-dimensional contrast image is summed over the entire depth and is presented as a one-dimensional line. The multiple images acquired over time create the two-dimensional contrast summation image over time for this sample. The left image shows vertical lines, which demonstrate the appearance of additional motion contrast noise within the BM-scan contrast image at that point in time. The right image shows the contrast summation images over time after the transverse motion removal method described above, for the case of $\alpha=0$. The variations in the vascular positions within the image over time are caused by the transverse motion occurring during imaging.

The phase noise estimation used for the numerical removal for the phase variance contrast images is based on the measured phase noise as a function of the reflectivity signal $S^2$. The measured OCT intensity signal $I^2$ is a combination of the reflectivity signal $S^2$ and the noise signal $N^2$. The averaged OCT intensity signal is of the form:

$$<|\tilde{I}|^2> = S^2 + <N^2>$$

The measured phase noise and the expected form are plotted on FIG. 21. For $S>>N$, the phase noise shows the expected form as described earlier.

Additional methods which can be used to remove the transverse motion noise involve using additional statistics to remove any contrast image containing transverse motion noise. Using an external motion trackers or software analysis of the OCT intensity and contrast images, BM-scan data containing significant transverse motion can be identified and removed. Repeating the BM-scan acquisition over the same region when less transverse motion is occurring eliminates the requirement of phase removal analysis.

Intermittent Flow Identification

One of the challenges of motion contrast screening is identifying regions that do not contain scatterers all of the time. OCT requires reflections within the sample to create the phase measurements and some situations do not allow for measurements to be taken at any time. The zebrafish and the segmental vessels are a good example of this reflectivity requirement. The segmental vessels are 7-12 microns in diameter for the 3 dpf (days post fertilization) embryo, which branch off of a larger vessel called the dorsal aorta. Confocal imaging of the embryo has shown that the blood cells are only present within specific locations of these vessels for a fraction of the time. If OCT imaging occurs at a transverse location when there are no blood cells present within the vessel, there is not enough reflectivity from within the vessel to produce a phase contrast signal.

FIG. 18 demonstrates multiple OCT images taken through the tail and yolk sac of the zebrafish at the same transverse scan location but at different time points. The arrows in all of the images designate the expected locations of the flow regions: the dorsal aorta (DA), the axial vein (AV), the segmental vessels (Se) and the dorsal longitudinal vessel (DLV). The locations of these flow regions is not evident through the OCT intensity image due to a lack of intensity contrast of these regions as well as a lack of sufficient absorption by these tiny vessels. The phase variance contrast images demonstrate the appearance of contrast for the dorsal aorta and the axial vein for all presented images, but the segmental vessels and the dorsal longitudinal vessel do not appear to have contrast at all times, as expected.

This situation is similar to the microvasculature in the retina, which also contains very small vasculature and does not contain motion contrast at all points in time. As with any random phenomenon, multiple visualization opportunities and increased statistics can assist in the visualization of the events. With the efficiency of the BM-scan acquisition, this method can be repeated over regions expecting an intermittent flow situation, such as microvasculature, in order to visualize the motion contrast.

Intensity/Speckle Contrast

All of the contrast analysis methods described so far have been directed towards the variance of phase changes over time for scatterers. With the same acquisition methods, there is available data of the OCT intensity information over time as well. Many types of sample properties can result in intensity fluctuations within the image: light coupling changes, source power fluctuations, and relative polarization changes in the interferometer all can cause intensity variations over time. Examples of intensity fluctuations caused by sample motion include, but are not limited to:

Interference of reflections from multiple scatterers located within the resolution of the system and small independent scatterers like might be found in blood.

Locations of flow based on variations in the reflecting constituents within the flow region over time.

Variations in absorption of regions of blood flow over time.

The intensity fluctuation and/or speckle analysis over time can act in parallel with the phase variance analysis work occurring for the same data acquired. In cases of high bulk transverse motion of the sample, the intensity analysis might be more useful in identifying locations of flow. One of the analysis techniques available with the temporal intensity information is the variance of the OCT intensity. In order to properly image this variance contrast, the result needs to be normalized based on the intensity information (e.g., the mean, the median, the maximum or the minimum of the intensity). Published intensity fluctuation and/or speckle analysis techniques use normalized spatial fluctuations in single images as contrast, limiting the spatial resolution of the contrast images. For a single time separation T of the intensity measurements, the variance of the intensity changes will identify contrast in regions of motion and absorption changes (listed above). The systematic intensity fluctuations mentioned earlier (e.g., coupling changes) also cause contrast to be observed in static regions of the image. One of the ways to try and reduce this unwanted fluctuation is to use numerical estimates of the expected fluctuations based on the OCT intensity and the structure of the sample. One form of contrast with an estimated form of intensity fluctuations is:

$$(\sigma_{\Delta t}^2(z_i,T) - f(z_i,I^2(z_i)))/<I^2>$$

Another analysis technique for the intensity fluctuation temporal information is to analyze using a Fourier transform to determine the temporal distribution of the fluctuations. The shape, width and amplitude of the spectral information from the Fourier transform can be used to identify multiple mobility parameters including but not limited to the average diameter of scatterer size and diffusional constant.

BRIEF DESCRIPTION OF THE FIGURES

FIG. 8A is a phase variance contrast image for maximum phase change time separation of $T_2=40T_1$ and FIG. 8B is a phase variance contrast image for maximum phase change time separation of $T_2=20T_1$.

FIG. 11A illustrates a schematic of transverse scan patterns for a MB-scan. FIG. 11B illustrates a schematic of transverse scan patterns for a BM-scan.

FIG. 13A illustrates a BM-scan acquired over a Zebrafish tail in the form of an OCT intensity image. FIG. 13B illustrates a BM-scan acquired over a Zebrafish tail in the form of a phase variance contrast image. The image size for both FIGS. 13A and B is 815 μm by 325 μm. Phase error removed in FIG. 13B, the contrast image, was numerically estimated to be $T_2=40$ ms in this case. Note that the image scale of the phase variance contrast image is 4 times larger than in the MB-scan contrast image of FIG. 12B.

FIG. 14B, the phase contrast image, is taken from a time point experiencing very little bulk transverse motion.

FIG. 16A illustrates an uncorrected large transverse motion case and FIG. 16B illustrates a corrected large transverse motion case with $\alpha=0$ chosen.

FIG. 17A is an image before the additional motion compensation for the $\alpha=0$ case and FIG. 17B is an image after the additional motion compensation for the $\alpha=0$ case.

FIG. 18A illustrates a BM-scan averaged OCT intensity image and FIGS. 18 B, C, and D show three-phase variance contrast images acquired at different time points. Each image was acquired within a total time of 50 ms. The arrows correspond to locations of the dorsal longitudinal vessel, two different segmental vessels (Se), the dorsal aorta (DA), and the axial vein (AV).

FIG. 19(A), a brightfield microscopy image, and FIG. 19(B), an image of a 3 dpf zebrafish, both show the expected anatomical features of the zebrafish. The lines drawn in FIGS. 19(A) and 19(B) are representative OCT image scan positions. Further analysis into the average flow and phase variations can improve the quality of these images.

FIGS. 23A, B, C, and D illustrate several contrast images produced using the MB-scan acquisition method of data over the zebrafish tail. FIG. 23A is an OCT intensity image showing structural information. The arrows in FIG. 23A depict the expected regions of motion for the image, corresponding to the two main blood vessels, the dorsal aorta and axial vein, along the fish. FIG. 23B is a phase variance contrast image that uses $T_2=1$ ms and $T_1=40$ μs with a variance scale of 0 to 2 radians$^2$ and observes the locations which are not visible on the Doppler OCT images until sufficient statistics make it just visible enough to be observed. The arrows in FIG. 23B depict the expected regions of motion for the image. FIG. 23C is a Doppler flow image that uses a scale of ±0.12 radians=±200 μm/s for the cases of 5 phase change averages. FIG. 23D is a Doppler flow image that uses a scale of ±0.12 radians=±200 μm/s for the cases of 100 phase change averages. Even with the improved visualization created with the increased statistics, prior knowledge of motion locations assists in the visualization.

FIG. 24A is the averaged OCT intensity image compared against FIG. 24B the phase variance contrast image, using 5 total B-scans, a rank 1 median filter in each direction, and a variance scale of 0 to 3 radians$^2$. The arrows in each of the images correspond to identified locations of dorsal aorta and axial vein.

FIG. 27A is an OCT intensity summation image is presented in logarithmic scale.

FIG. 28B, the Doppler flow image, does not use any thresholds and has a scale which corresponds to ±2.5 mm/s. Fast flow within the major retinal vessels is observed in the axial flow measurement, but choroidal flow is not observed using this image analysis technique. FIG. 28A demonstrates phase variance contrast images for a variety of phase change time separations. The increase in time separation corresponds to an increase in vascular visualization (choroidal vessels) as well as an increase in contrast shadowing below vasculature. The increased time separation also corresponds to an increased sensitivity to transverse motion, causing some vertical lines of contrast.

FIG. 29A is a MB-scan phase variance contrast for the case of 40 µs time separation with 10 phase changes to calculate variance. FIG. 29B is a MB-scan phase variance contrast for the case of 160 µs time separation with 40 phase changes to calculate variance. FIG. 29C is an MB-scan phase variance contrast for the cases of 240 µs time separation with 40 phase changes to calculate variance. FIG. 29D is a MB-scan phase variance contrast for the case of 320 µs time separation with 40 phase changes to calculate variance. The images in FIGS. 29A, B, C, and D demonstrate the flattening of the retina used to remove the curvature of the images associated with changes of optical path length with the curvature of the globe of the mouse eye. Flattening of the retinal images and retinal layer separation through boundary identification in images are the two main ways to extract information from depth regions in the three-dimensional intensity and contrast data to create transverse or en face images from the data set.

FIG. 31A is the averaged intensity image.

FIG. 35A, the intensity image, was summed over the entire retina, while FIG. 35B, the contrast image, was summed over the top half of the retina for the 200 transverse pixel BM-scan data across retina. FIG. 35B, the contrast image, is a single 200×51 pixel image created by summing the top of the retina from a single acquisition over the retina. The arrows identify some of the smaller visible blood vessels.

FIGS. 36A, B, C, and D show four en face phase contrast summation images created from the top of the retinal data acquired from the repeating 100 transverse pixel BM-scan method. The images show 100×50 pixel images extrapolated to 100×100 of contrast summation over the top of the retina, acquired successively during a single BM-scan acquisition of the system. The arrows highlight some of the microvasculature which is visible in that given image which does not appear in all of the other images due to the intermittent nature of the contrast. The transverse scan region of the image is identical to the region of the image in FIGS. 34A and 34B.

Figure 1:
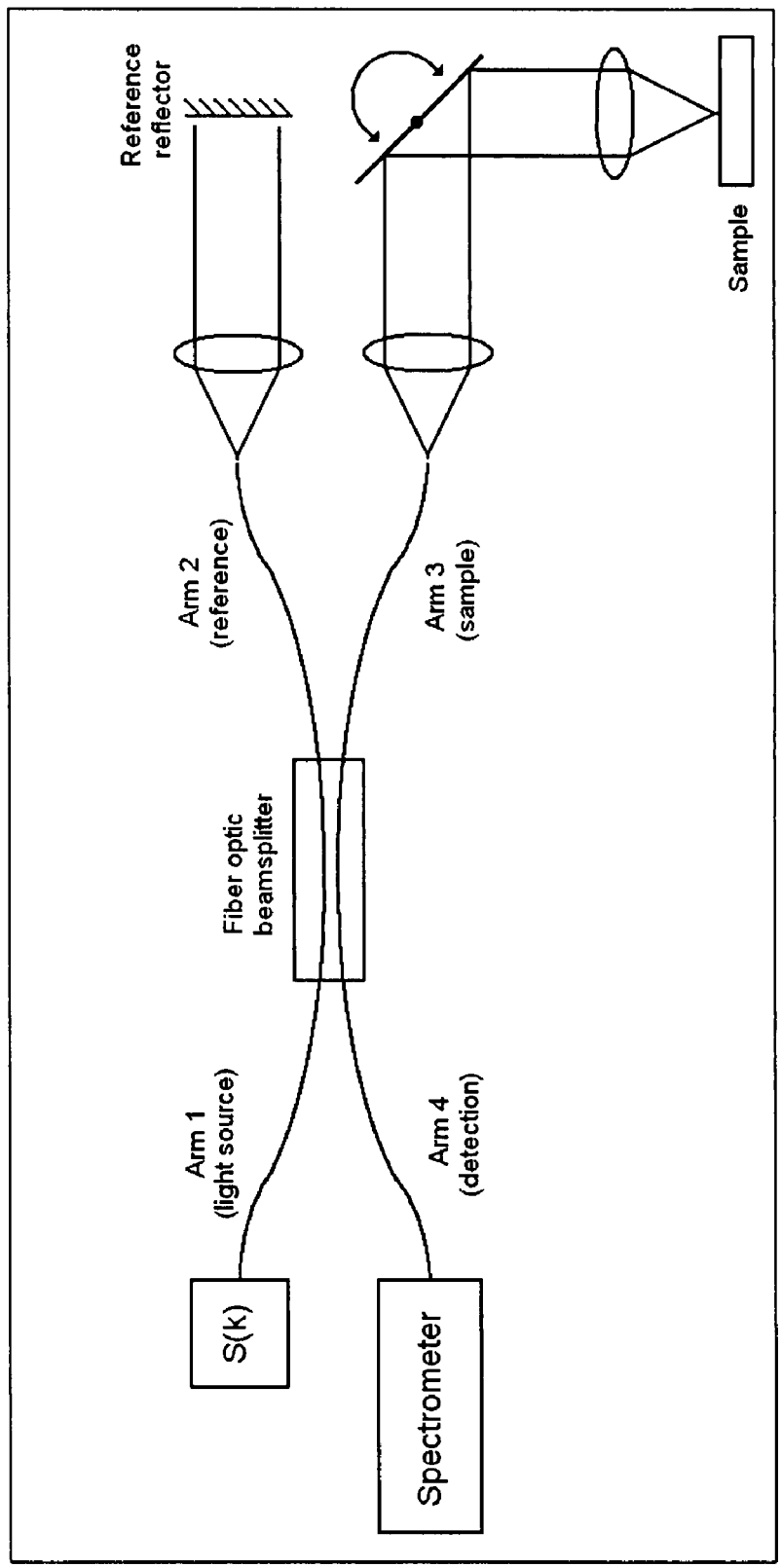
FIG. 1 illustrates a basic SDOCT system schematic representative of the system used for most of data presented herein. The low coherence light source $S(k)$ is split between the reference and sample arms of the fiber interferometer. The reflected light is collected and measured in the spectrometer, from which the depth reflectivity profile is calculated.
Figure 2:
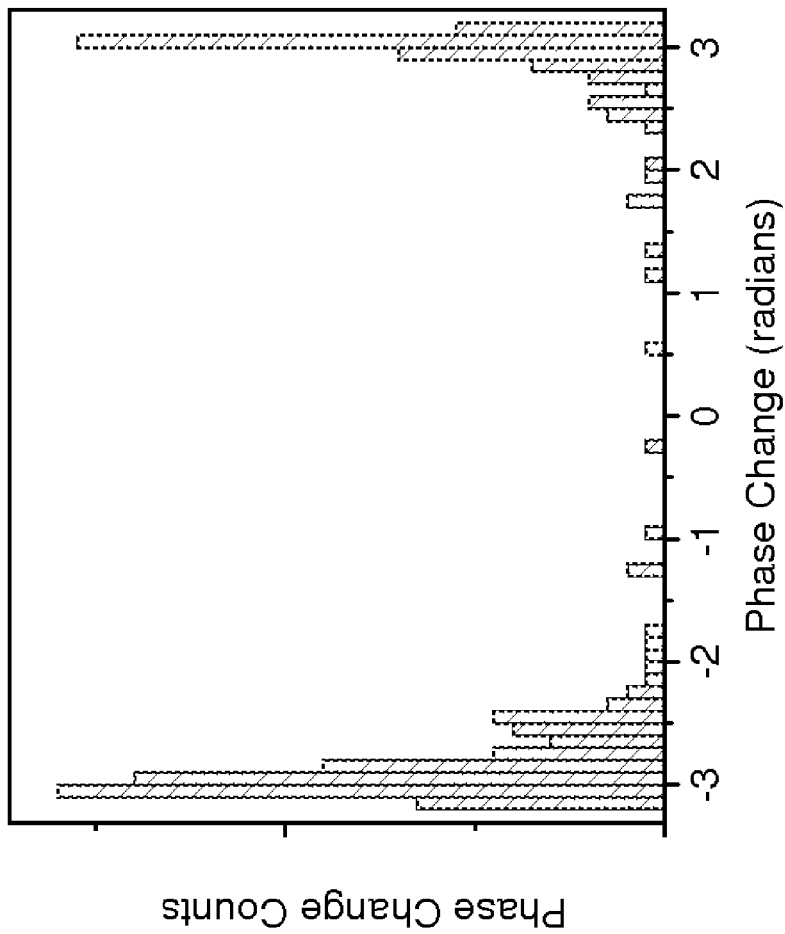
FIG. 2 shows simulated phase change data for bulk motion of ~$\pi$ radians (~one quarter of the wavelength of the imaging light).
Figure 3:
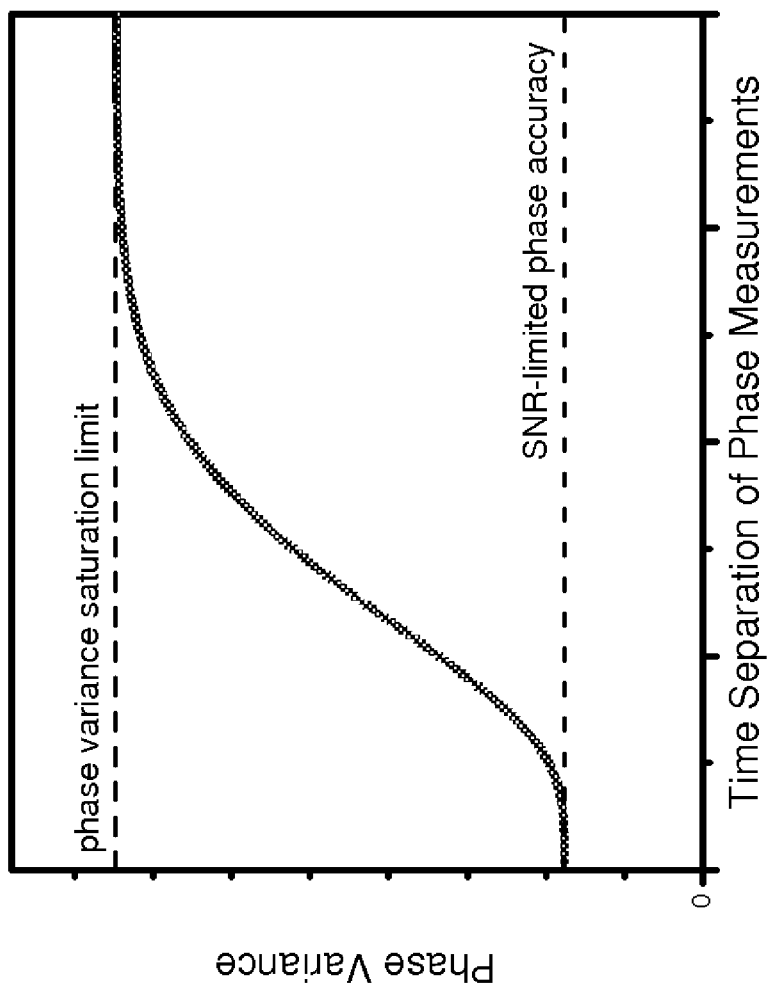
FIG. 3 is a schematic description of expected phase variance measurements for mobile scatterers for a range of time separations of phase change measurements.
Figure 4B:
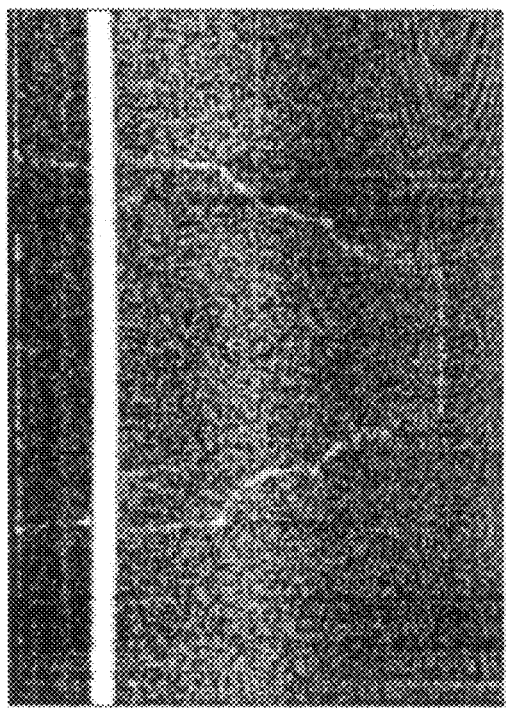
FIG. 4A illustrates a schematic of a sample corresponding with the non-averaged OCT intensity image shown in FIG. 4B. To obtain the images, a 2% Agarose well is filled with intensity-matched 0.1% Intralipid solution. The intensity contrast within the image is limited only to the edges of the wells and the air-water interface.
Figure 4A:
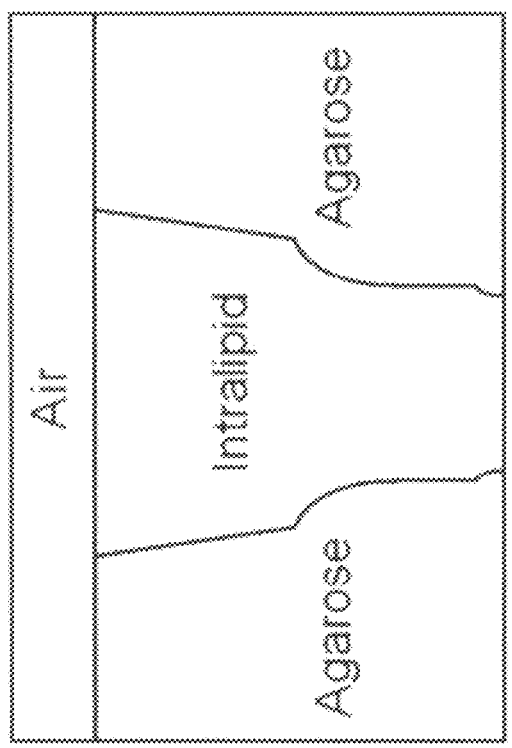
Figure 5B:
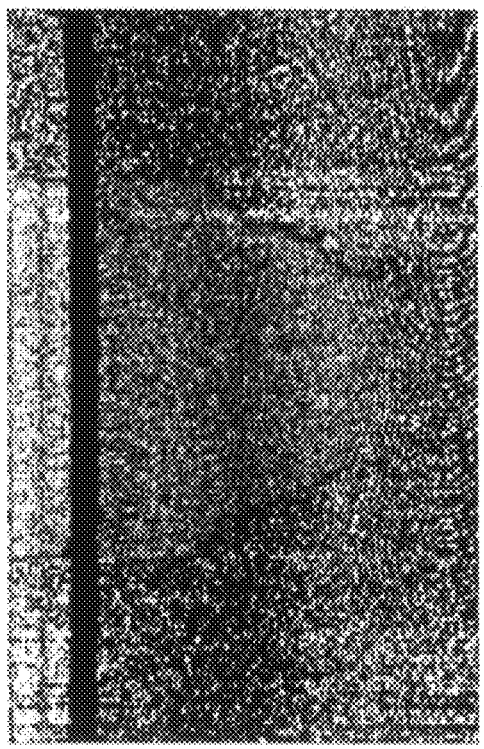
FIG. 5A is a phase variance image for phase change time separation of T=40 μs and FIG. 5B is a phase variance image for phase change time separation of T=80 μs.
Figure 5A:
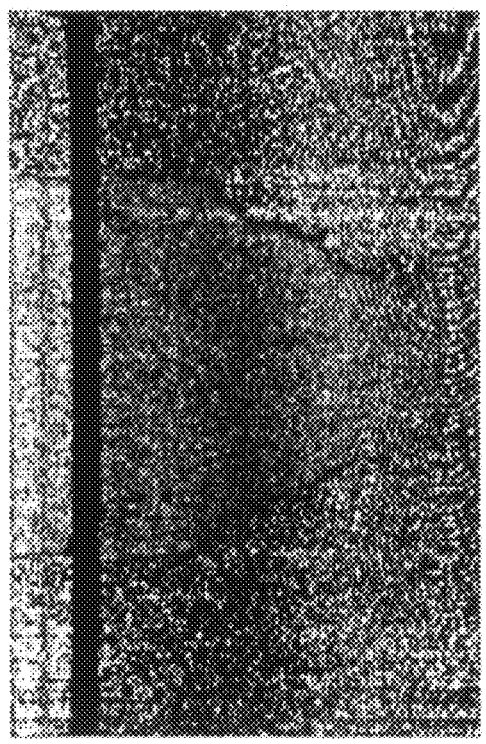
Figure 6A:
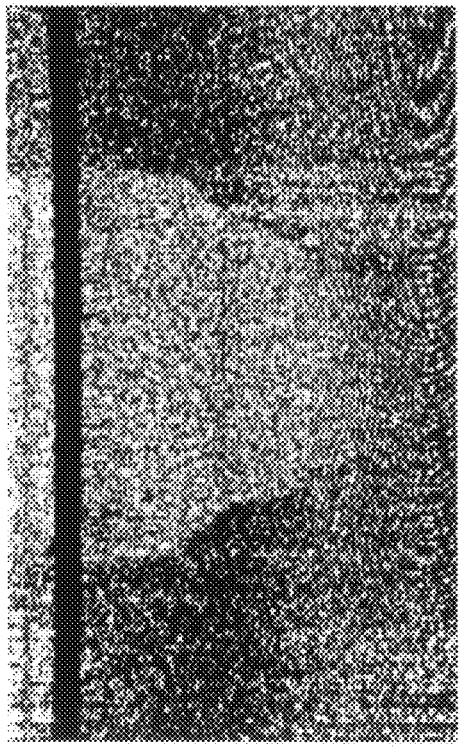
FIG. 6A is a phase variance image for phase change time separation of T=200 μs and FIG. 6B is a phase variance image for phase change time separation of T=400 μs.
Figure 6B:
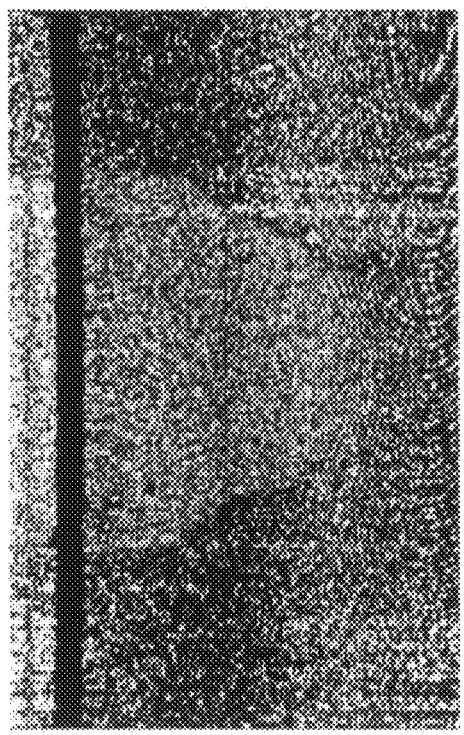
Figure 7B:
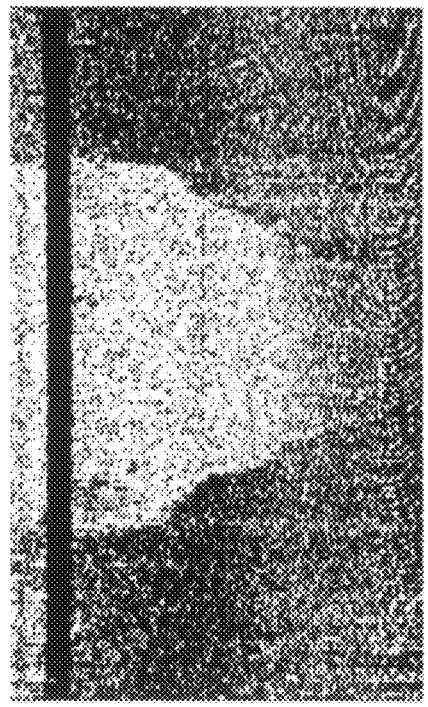
FIG. 7A is a phase variance image for phase change time separation of T=800 μs and FIG. 7B is a phase variance image for phase change time separation of T=1.6 ms.
Figure 7A:
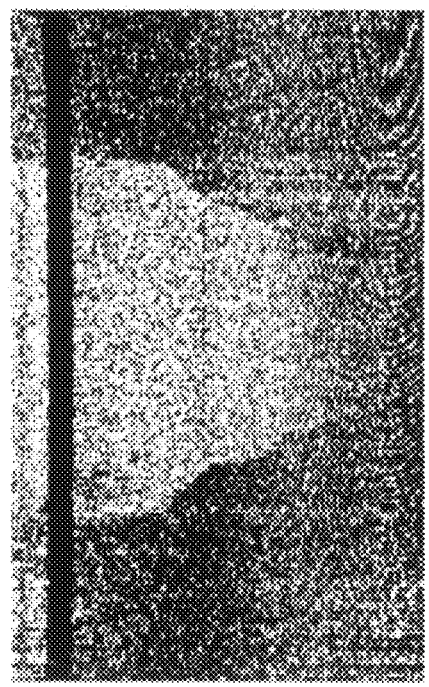
Figure 9B:
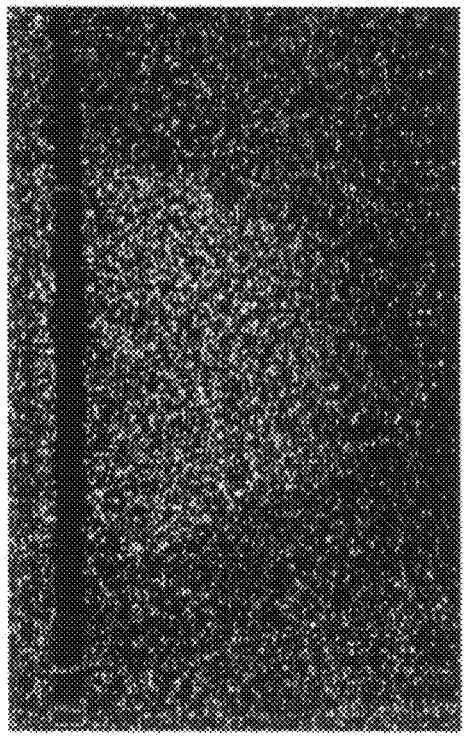
FIG. 9A is a phase variance contrast image for a maximum phase time separation of $T_2=10T_1$ and FIG. 9B is a phase variance contrast image for a maximum phase time separation of $T_2=5T_1$.
Figure 9A:
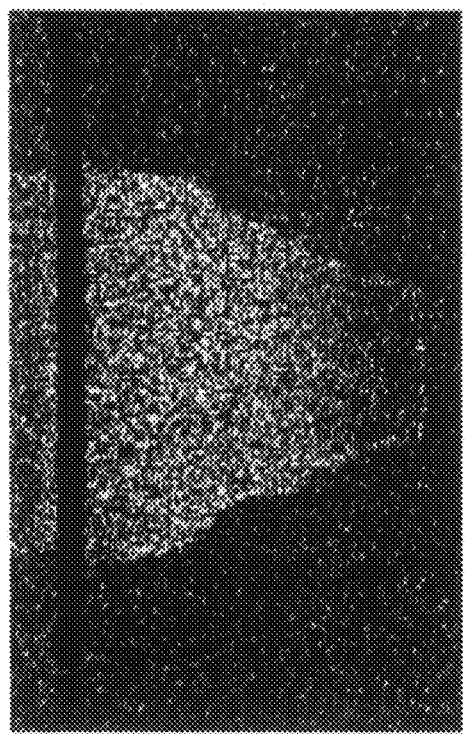
Figure 10:
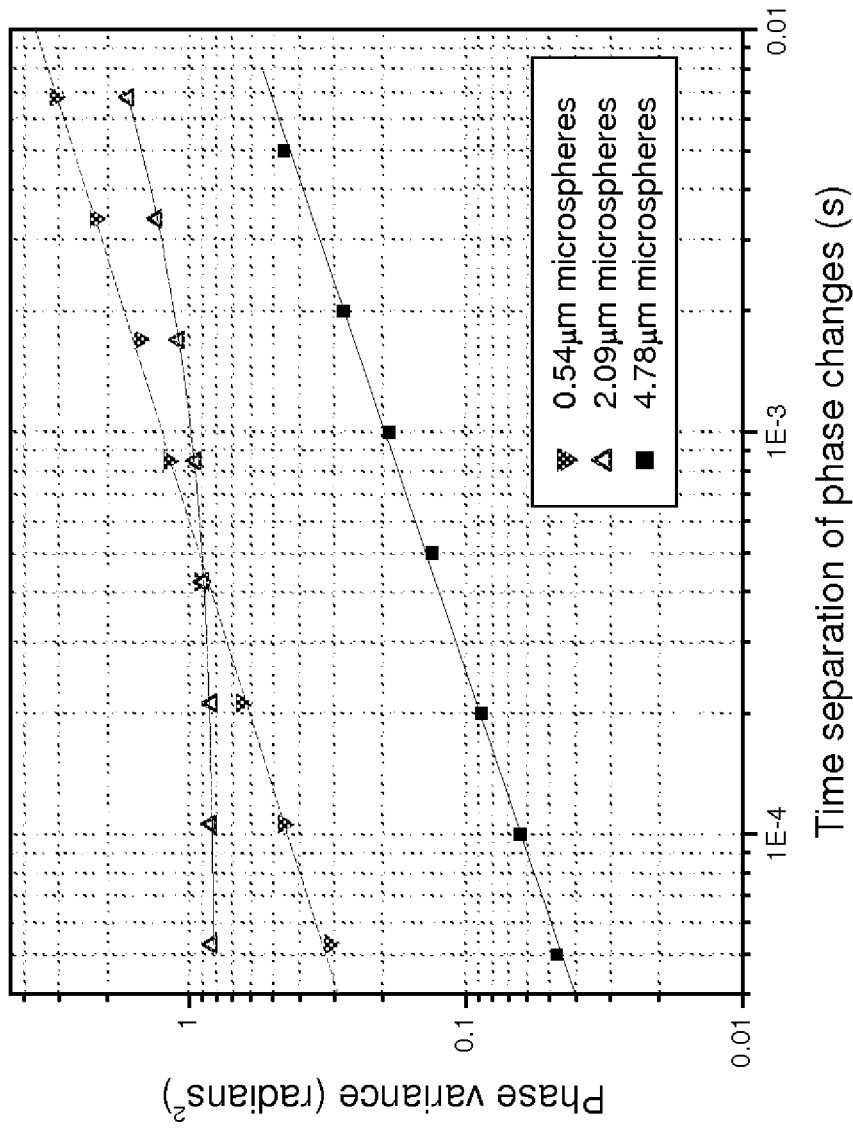
FIG. 10 shows phase variance data for a single scatterer in water. Displayed data is for spheres of diameter 0.5 μm, 2 μm and 5 μm. The 2 μm case demonstrates the effect of a phase error due to a low OCT signal on the phase variance data from expected form.
Figure 12A:
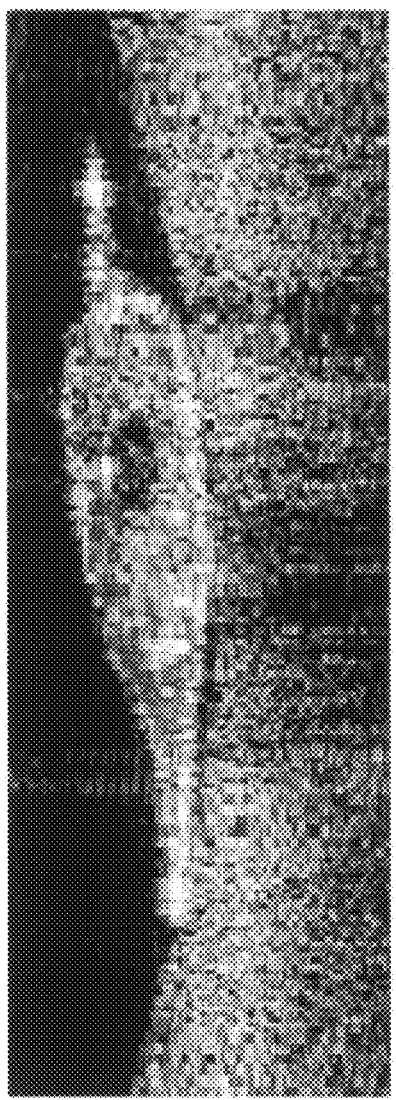
FIG. 12A illustrates a MB-scan acquired over Zebrafish tail in the form of an OCT intensity image.
Figure 12B:
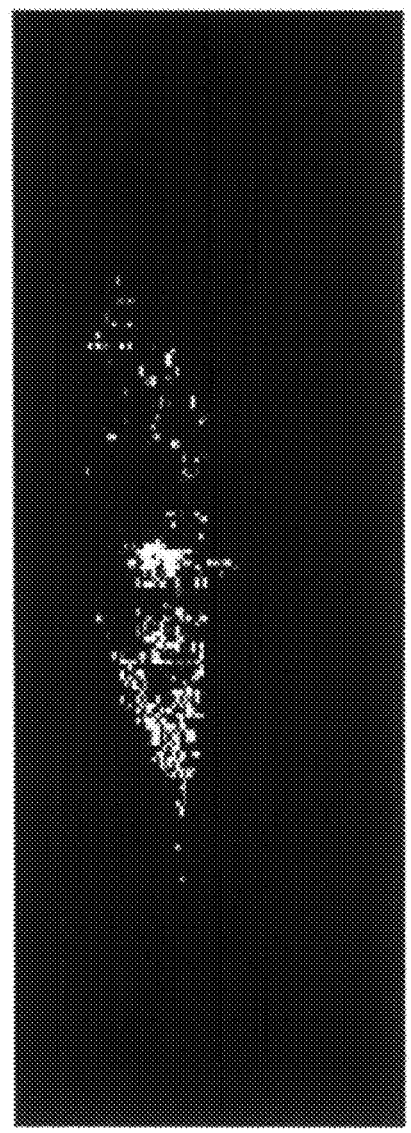
FIG. 12B illustrates a MB-scan acquired over Zebrafish tail in the form of a phase variance contrast image. Image sizes are 900 μm by 325 μm. $T_2=1$ ms and $T_1=40$ μs.
Figure 14A:
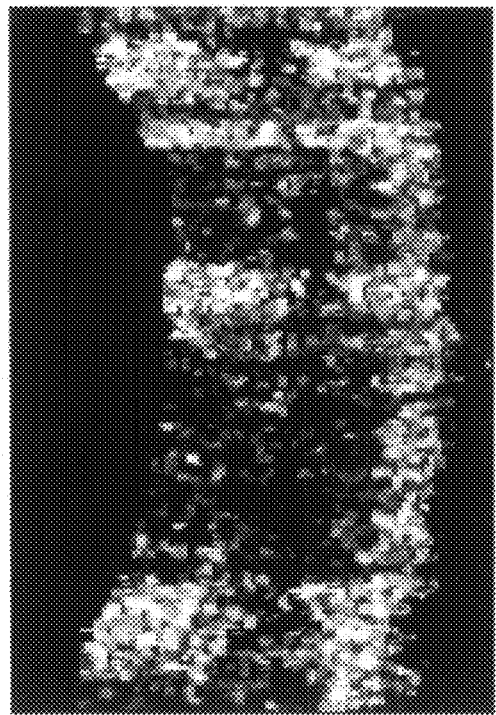
FIG. 14A illustrates the averaged intensity image calculated for a time point undergoing low transverse motion from BM-scan data for retina undergoing transverse motion.
Figure 14B:
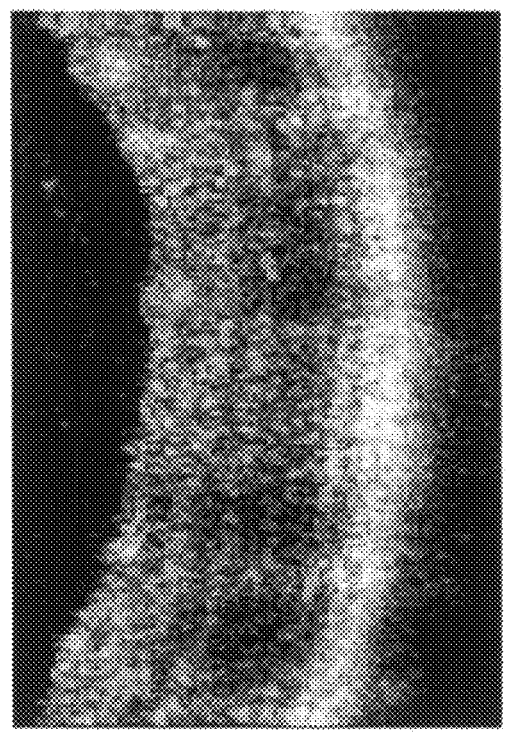
FIG. 14B illustrates the phase contrast image, after noise removal and median filtering, generated from BM-scan data for retina undergoing transverse motion.
Figure 15:
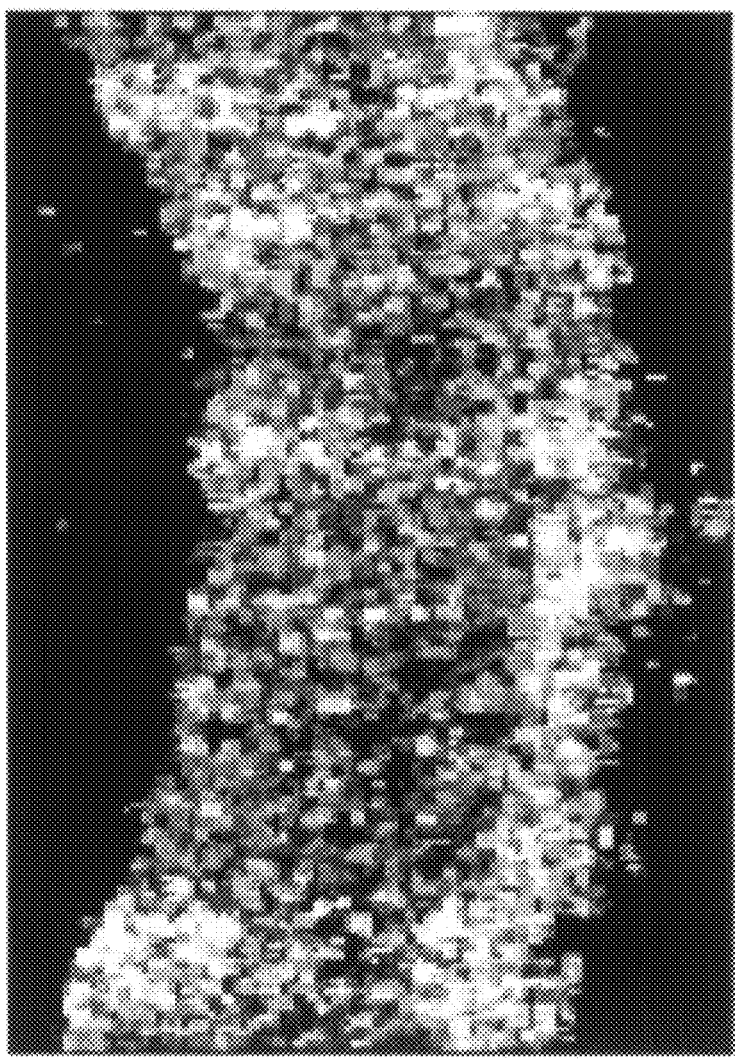
FIG. 15 illustrates a phase variance contrast image for the case of uncorrected large bulk transverse motion.
Figure 16A:
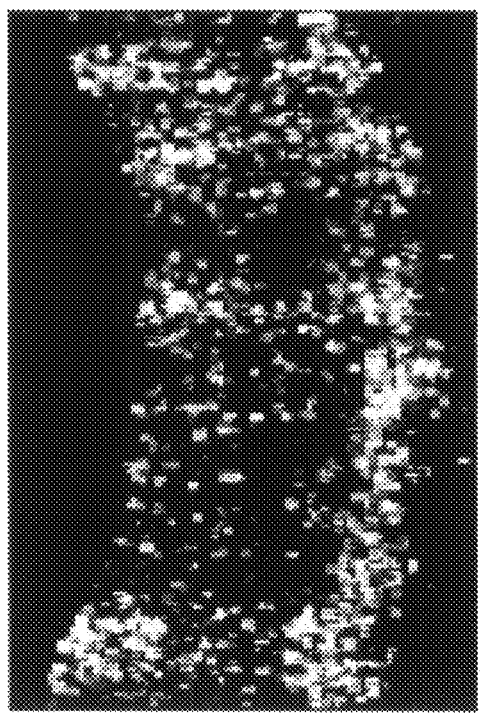
FIGS. 16A and B are a comparison of phase contrast images.
Figure 16B:
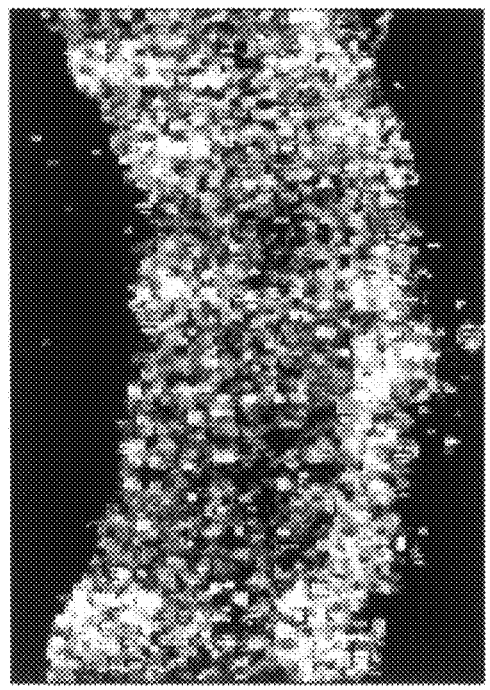
Figure 17B:
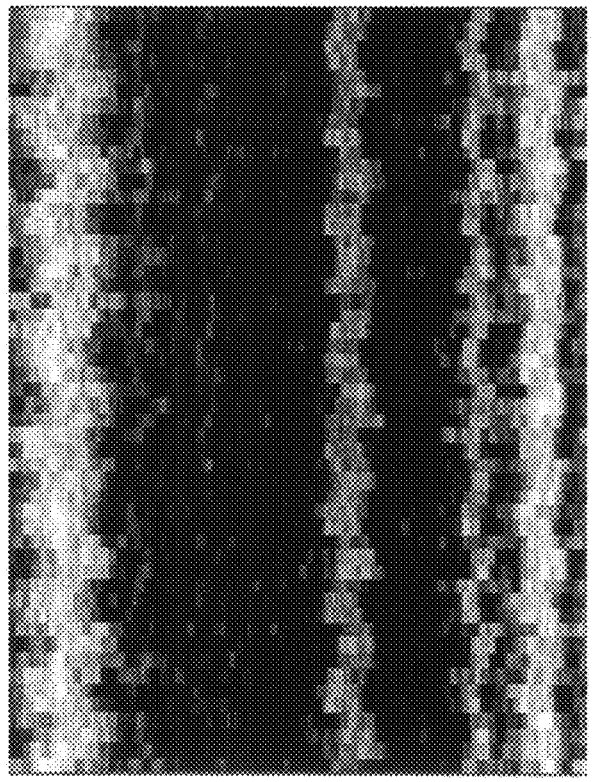
Figure 17A:
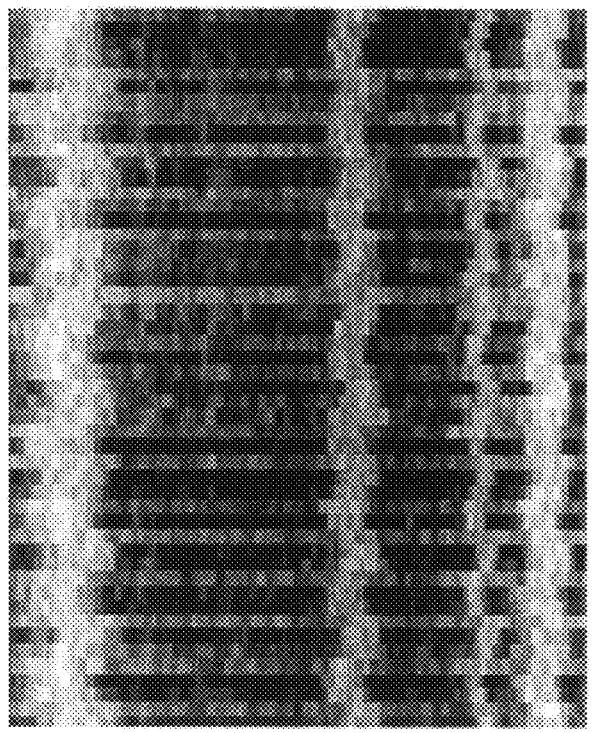
FIGS. 17A and B are contrast summation images over time summed over the full retinal depth, acquired over 2.6 s.
Figure 19A:
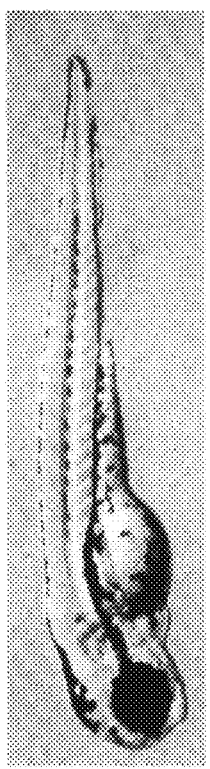
FIGS. 19A and B illustrate OCT imaging for the visualization of a 3 dpf zebrafish.
Figure 19B:
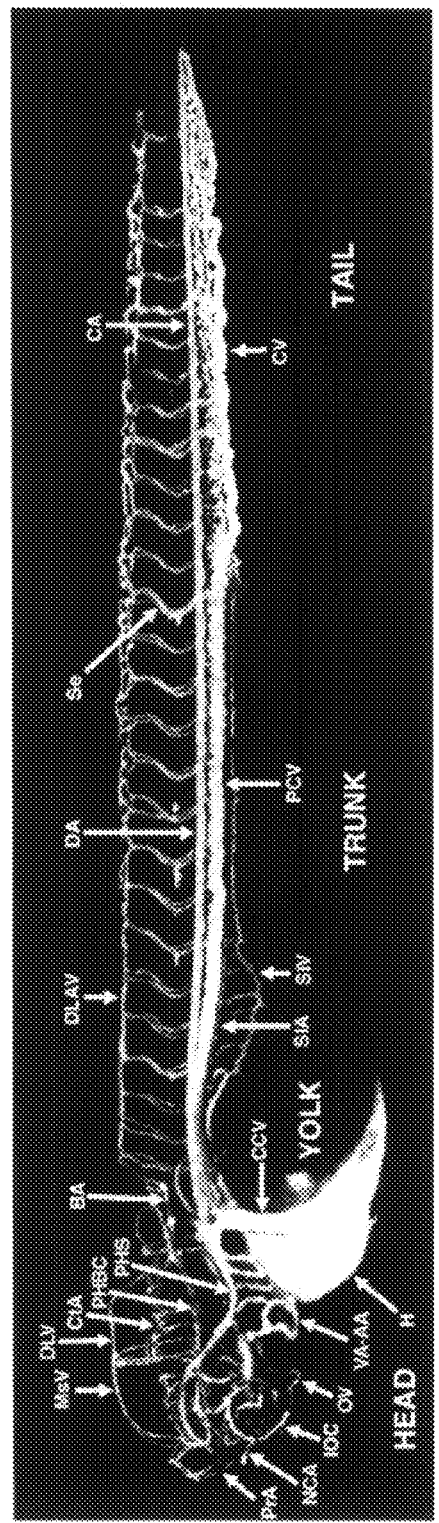
Figure 20B:
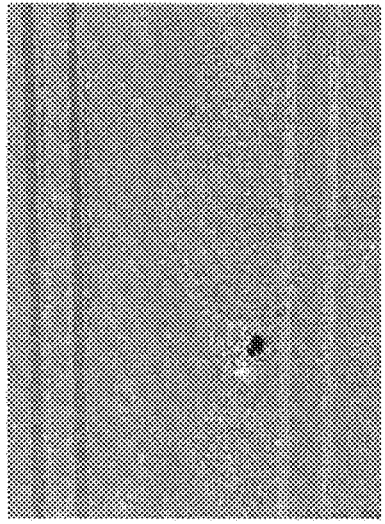
FIG. 20B shows the flow inside the heart after improved statistics reduce the phase noise low OCT signal pixels in the image.
Figure 20A:
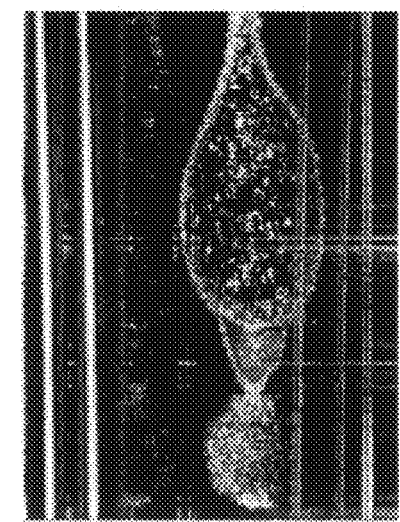
FIG. 20A depicts an OCT intensity image showing the internal structure of the zebrafish from FIG. 19.
Figure 20C:
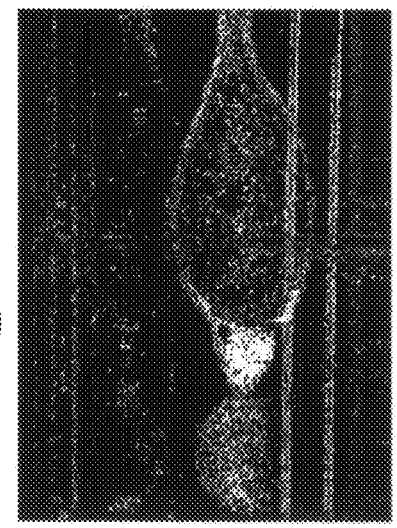
FIG. 20C depicts a phase contrast image using phase variance data after removing the phase error component. Note the clear appearance of the heart in FIG. 20(B) and the in-flow tracts on the yolk sack in FIG. 20(C) at the arrows, which matches with expected regions from FIG. 19(B).
Figure 21:
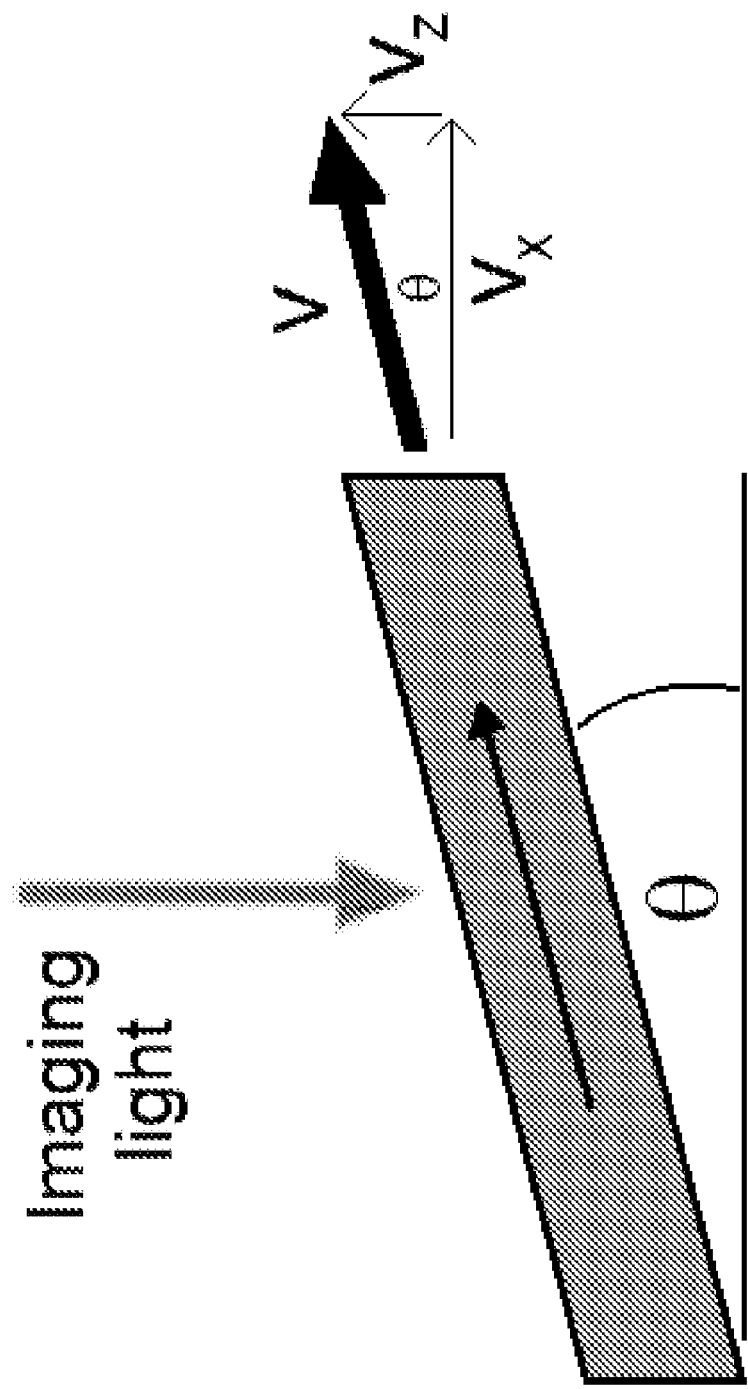
FIG. 21 is a schematic of the directionality of flow relative to the imaging light. The axial flow component observed by Doppler OCT techniques is designated by Vz.
Figure 22:
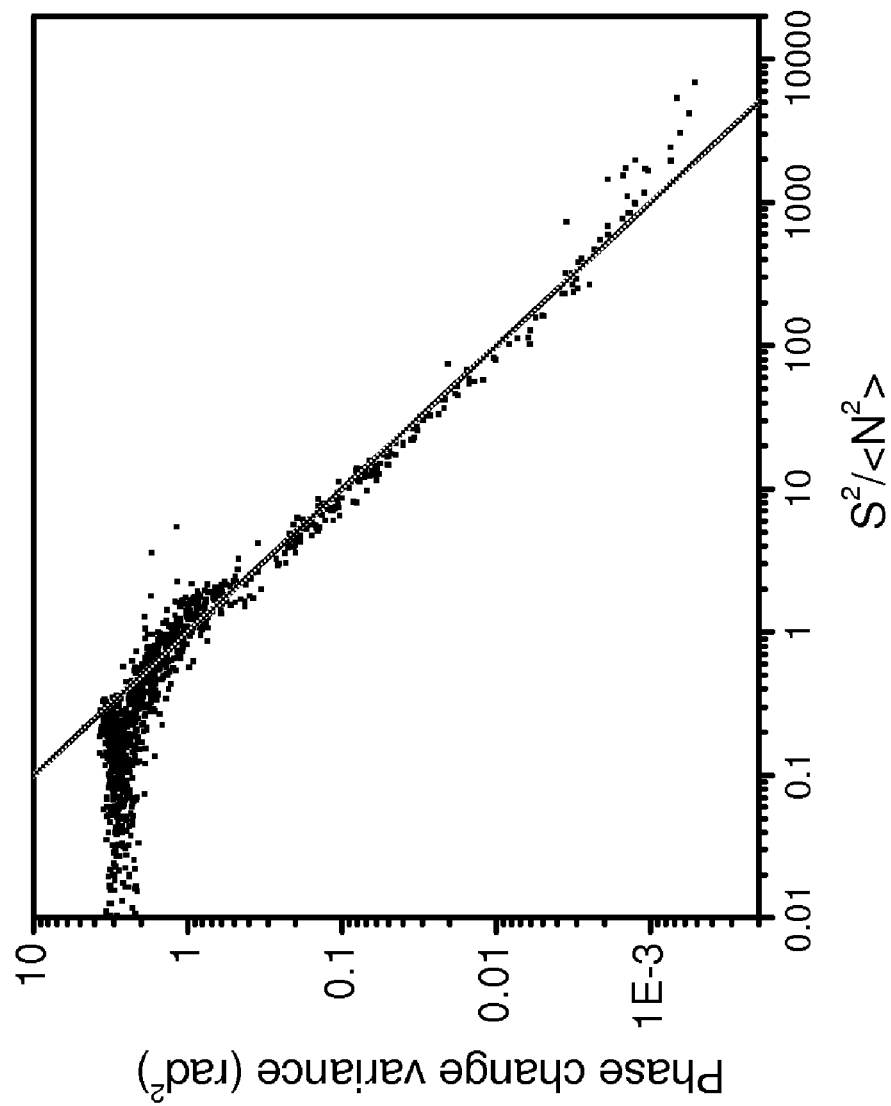
FIG. 22 is an SNR-limited phase noise plotted versus averaged OCT intensity signal.
Figure 24B:
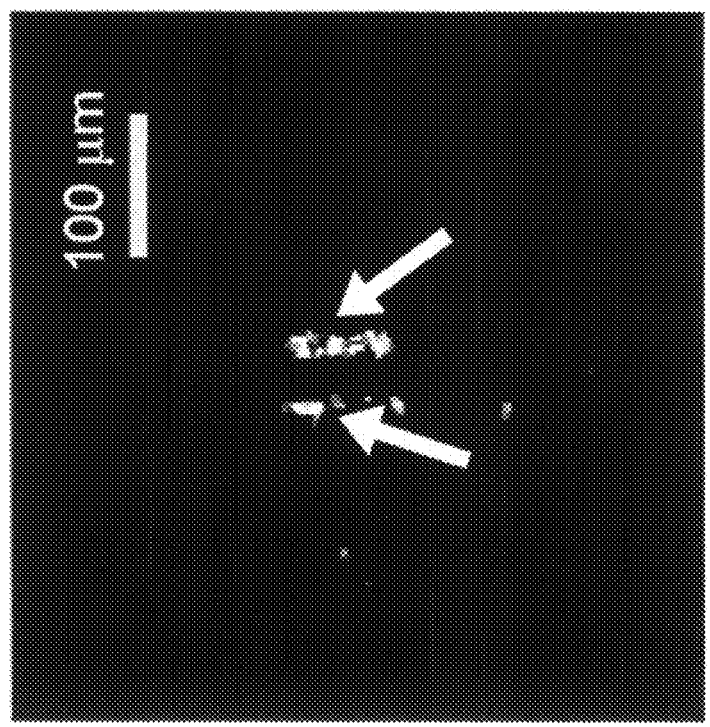
FIG. 24B, the phase variance contrast image, clearly observes the same motion regions as the MB-scan, but with additional shadowing below the vessels due to refractive index changes of the vasculature.
Figure 24A:
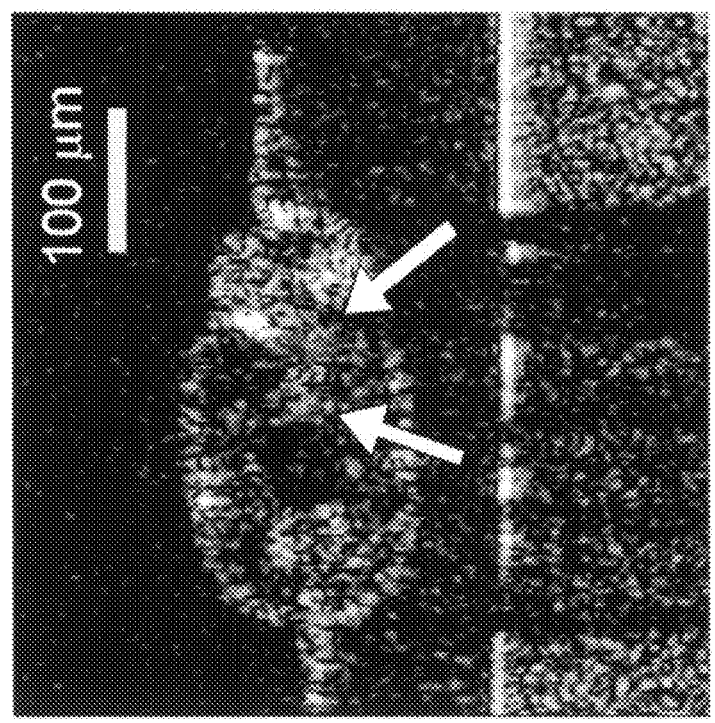
FIGS. 24A and B demonstrate the same region of the zebrafish as in FIGS. 23A, B, C, and D, however, they use the BM-scan acquisition method with a time separation of T=10 ms. The total time of the data acquired for the 200 transverse pixel image is 50 ms for the chosen parameters of the acquisition. Due to the reduced quantitative dynamic range of the Doppler OCT methods with this data, the images produced using that method are not presented.
Figure 25:
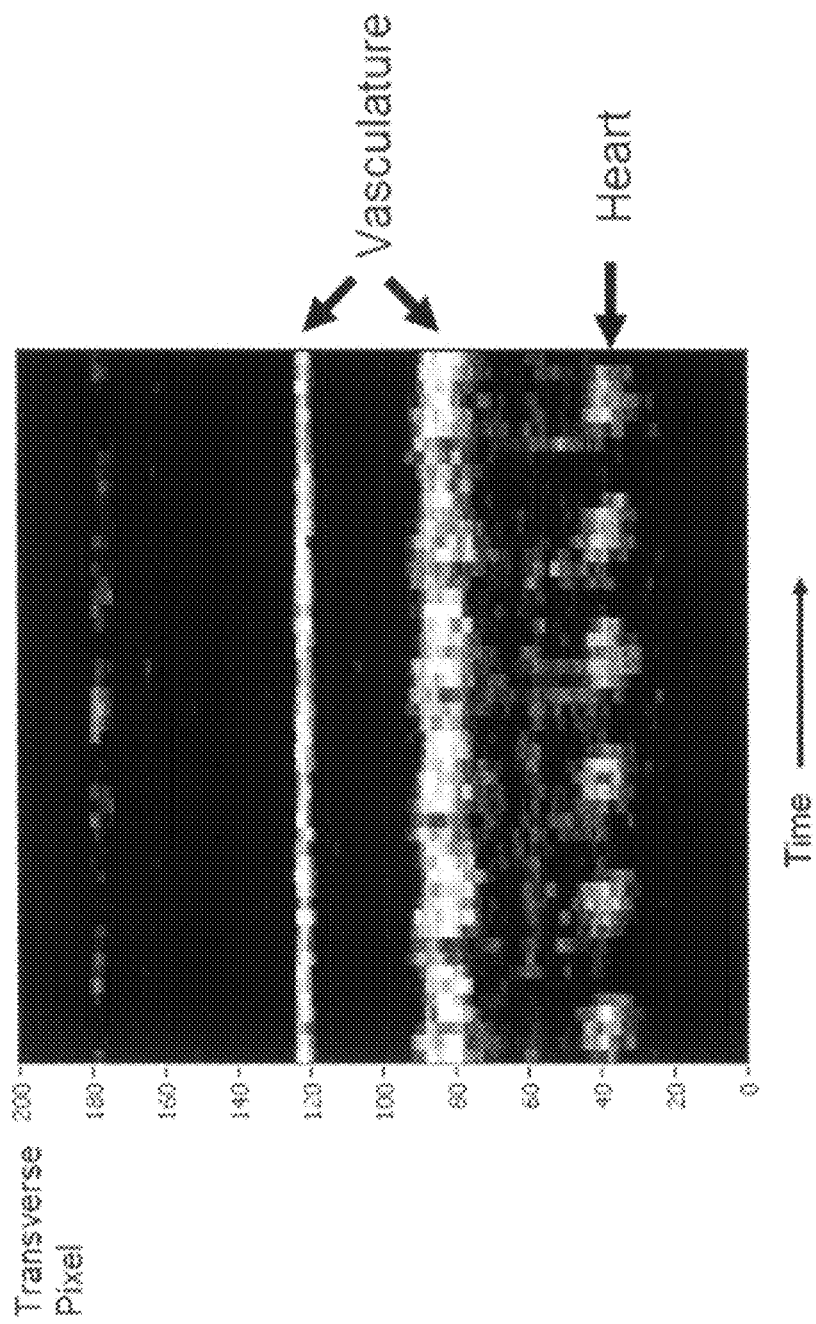
FIG. 25 displays a phase contrast summation image over time for a transverse slice located over the zebrafish heart for a total time of 2.6 s. Each time point is acquired in 50 ms. This method was also used in FIG. 17. The variations in the vasculature and in the heart can be clearly seen. The quantitative measure of the heart summation contrast change over time is shown in FIG. 26. The variations in contrast, which correspond to the changes in the size of the flow region as well as the changes in the flow observed within the region follow the expected heart rate of the zebrafish.
Figure 26:
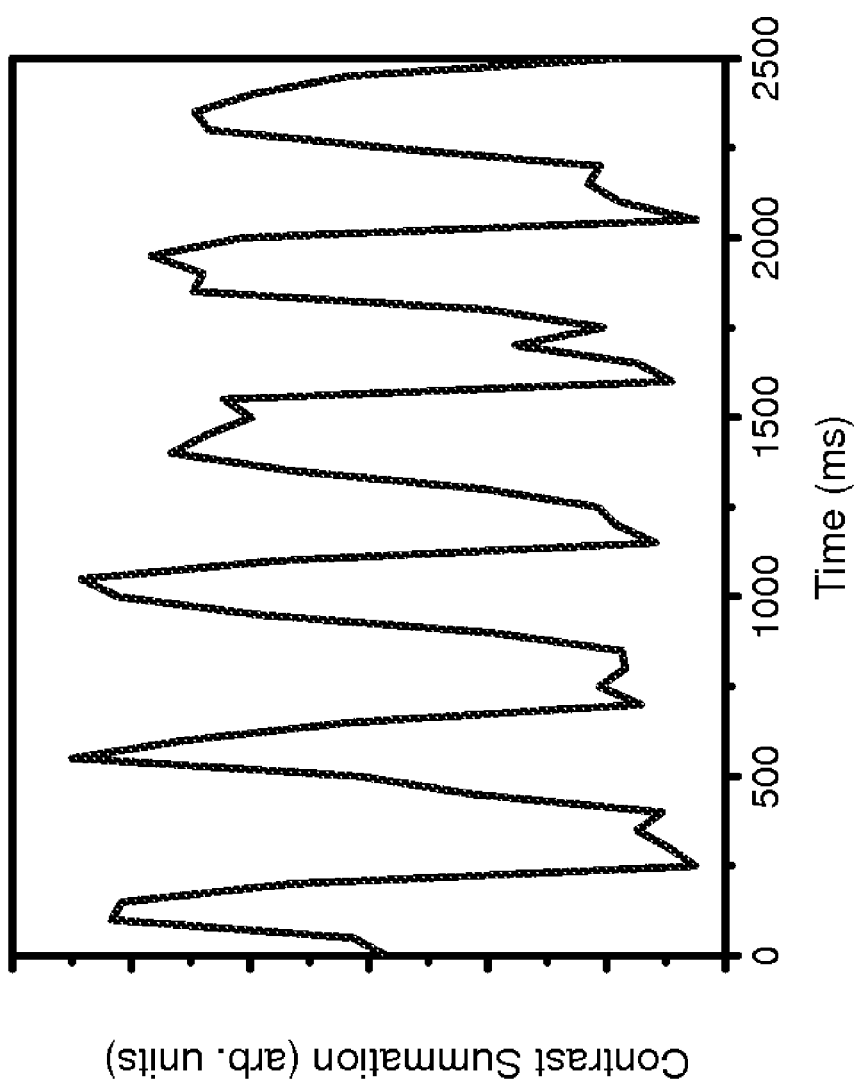
FIG. 26 illustrates contrast over time for the zebrafish heart at one transverse location. Contrast was summed over 3 transverse pixels (7.2 µm) and over the entire depth of the zebrafish.
Figure 27C:
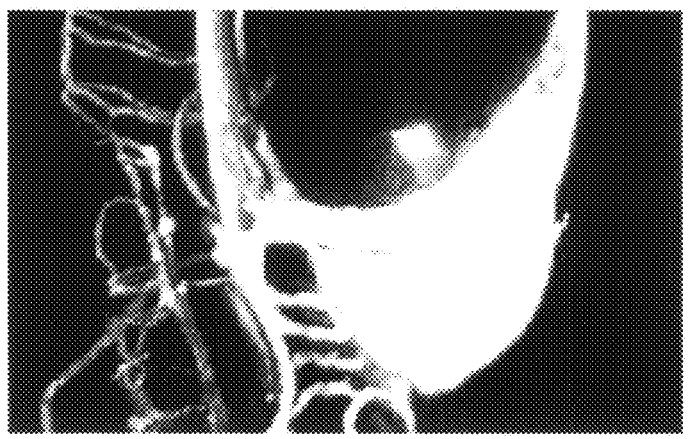
FIG. 27C, the confocal image of fluorescent dye injected in a similarly aged zebrafish, is shown as a correlation to the imaged vasculature within the motion contrast image, FIG. 27B.
Figure 27B:
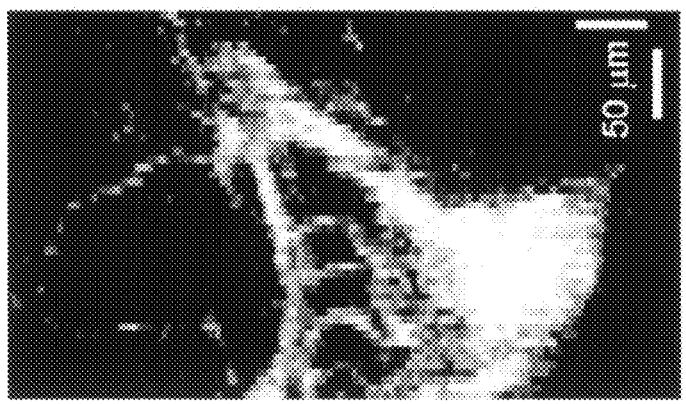
FIG. 27B is the phase variance summation image is presented in logarithmic scale to improve visualization for comparison with FIG. 27C, a similar region of a confocal image of GFP-labelled 3 dpf zebrafish.
Figure 27A:
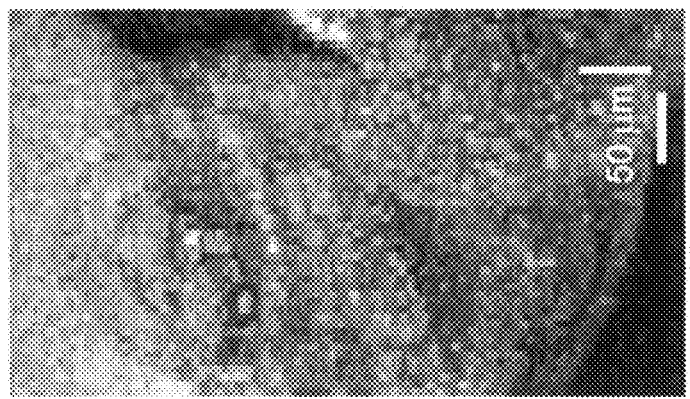
FIGS. 27A, B, and C are en face images over zebrafish heart.
Figure 28B:
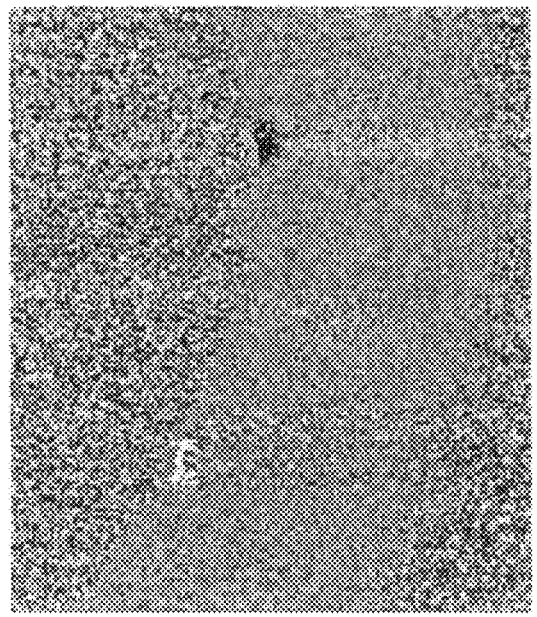
FIG. 28A demonstrates the averaged OCT intensity image and FIG. 28B shows the Doppler flow image from successive phase changes using 5 averages acquired over the mouse retina using the MB-scan.
Figure 28A:
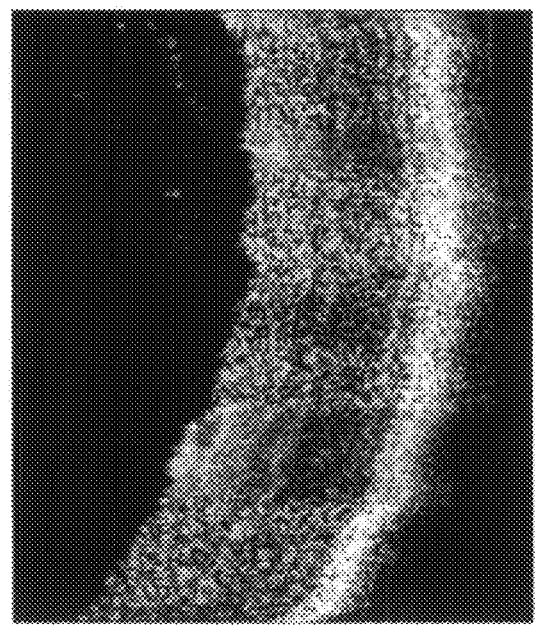
Figure 30B:
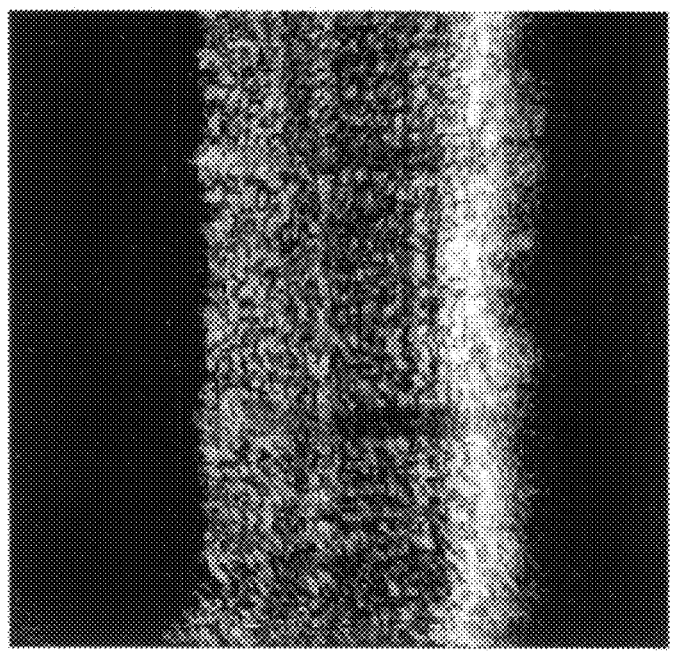
FIG. 30B illustrates an averaged B-scan intensity image after realignment to flatten retina.
Figure 30A:
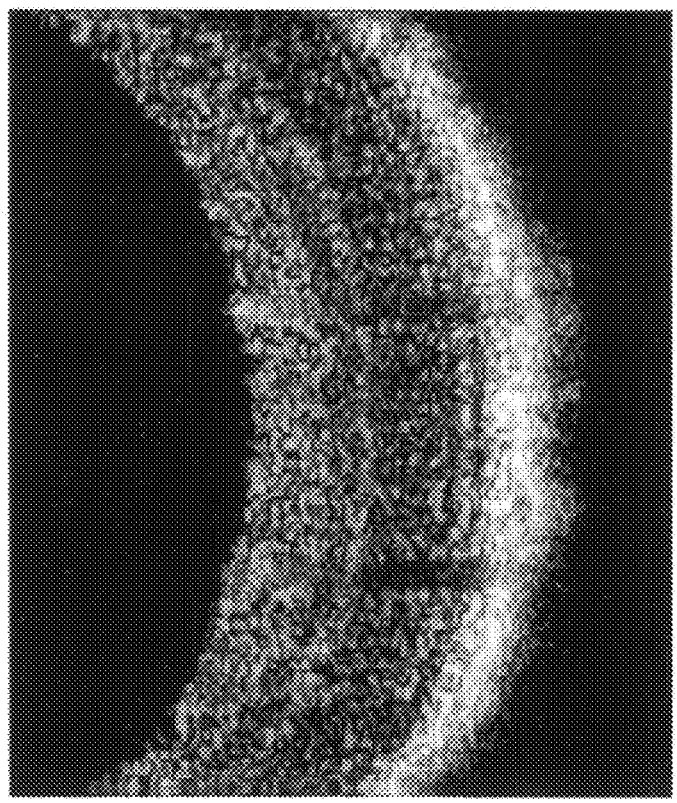
FIG. 30A illustrates an averaged B-scan intensity image before realignment to flatten retina.
Figure 31A:
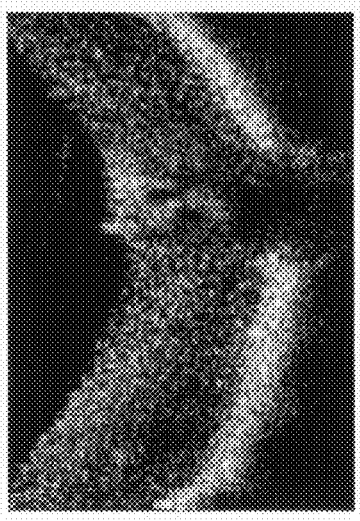
FIGS. 31A, B, and C show BM-scan images for mouse retina.
Figure 31C:
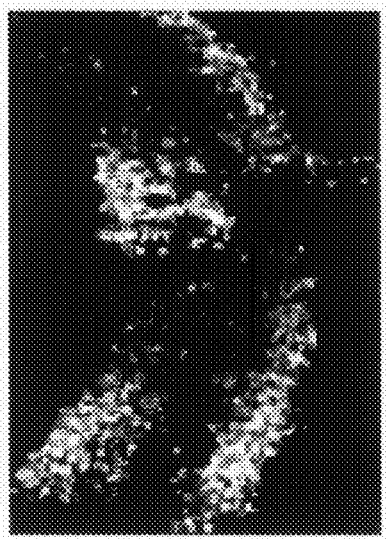
FIG. 31C is the phase variance contrast image after the application of noise removal and median filtering. The variance images use the scale 0 to 3 radians$^2$.
Figure 31B:
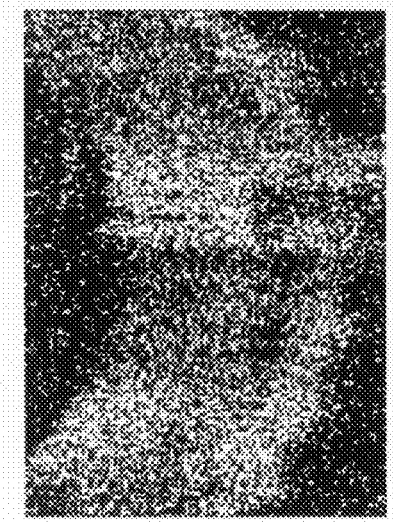
FIG. 31B is the phase variance image without any numerical phase error removal or image filtering.
Figure 32B:
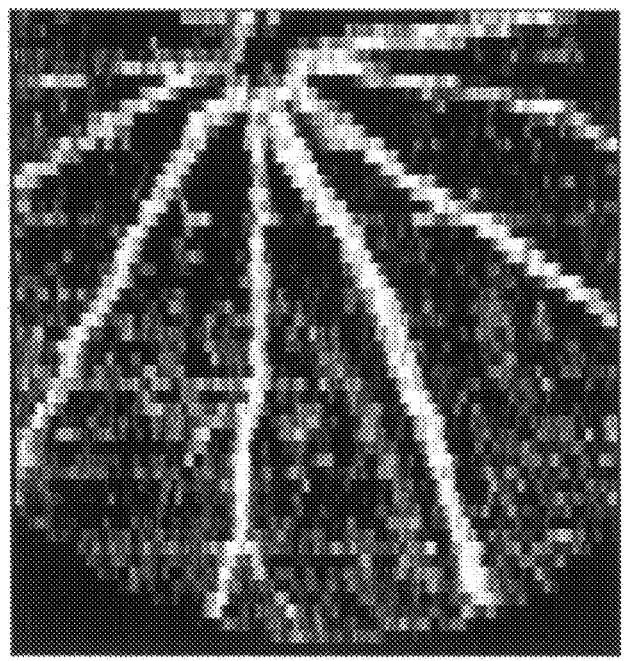
FIG. 32B displays a BM-scan en face phase contrast image summed over the entire retina.
Figure 32A:
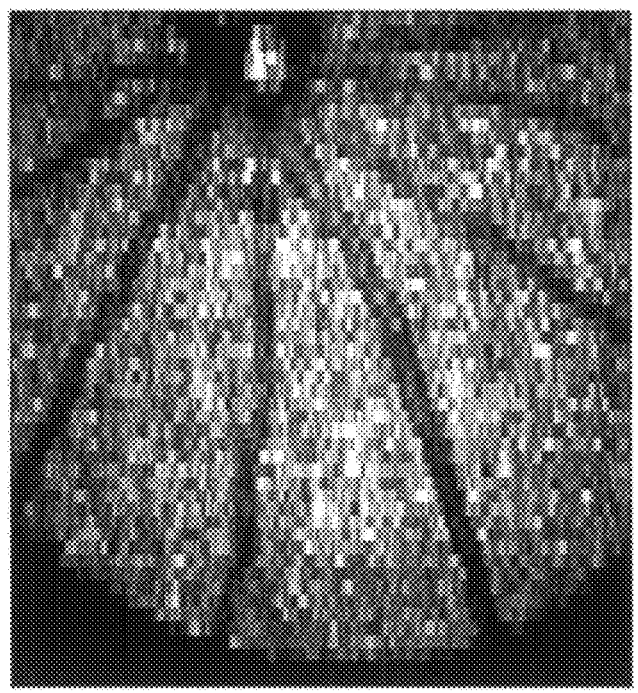
FIG. 32A displays a BM-scan en face intensity image summed over the entire retina.
Figure 33B:
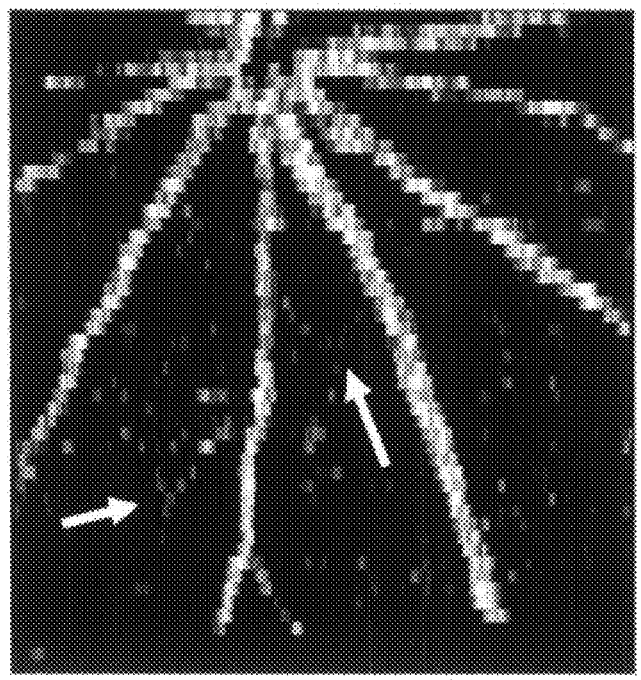
FIG. 33B, the contrast image, corresponds to the surface retinal vessels. The arrows correspond to locations of identified microvasculature.
Figure 33A:
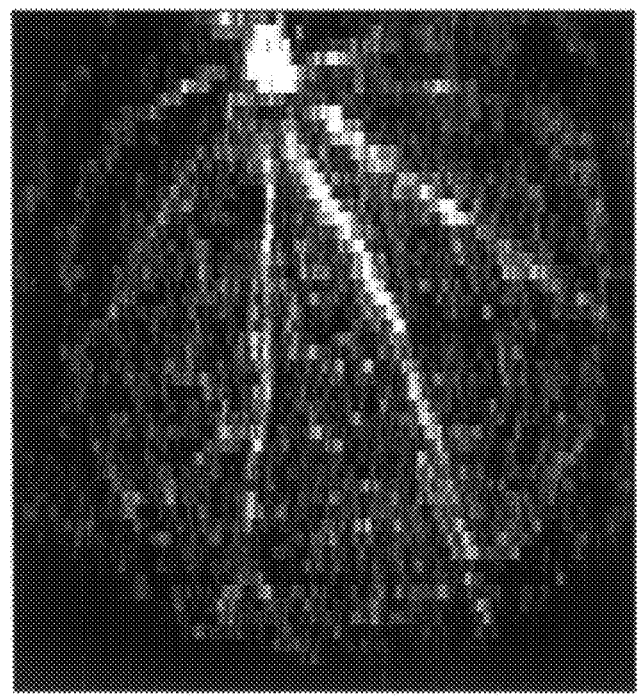
FIG. 33A displays en face summation image of the intensity and FIG. 33B displays the phase variance contrast, with summation chosen to be over only the top half of the retina.
Figure 34B:
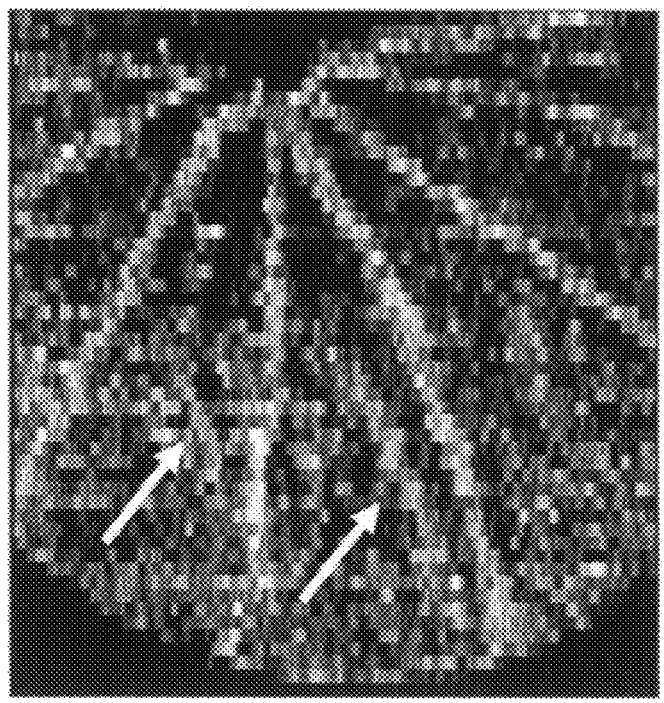
FIG. 34B, the contrast image, corresponds to the choroidal vessels as well as the shadowing contrast of the major retinal vessels. The arrows correspond to locations of identified microvasculature.
Figure 34A:
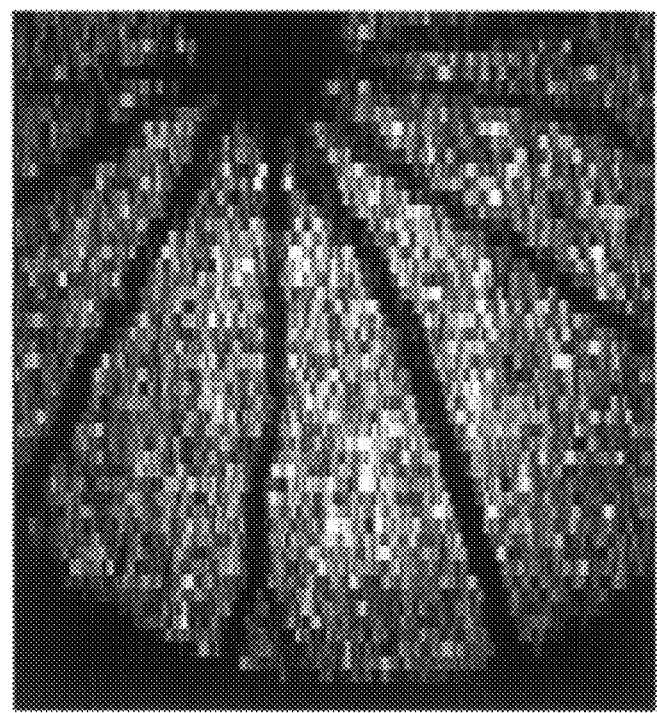
FIG. 34A displays en face depth summation images of the intensity and FIG. 34B displays the phase variance contrast, summed over the bottom half (choroidal region) of the retina.
Figure 35B:
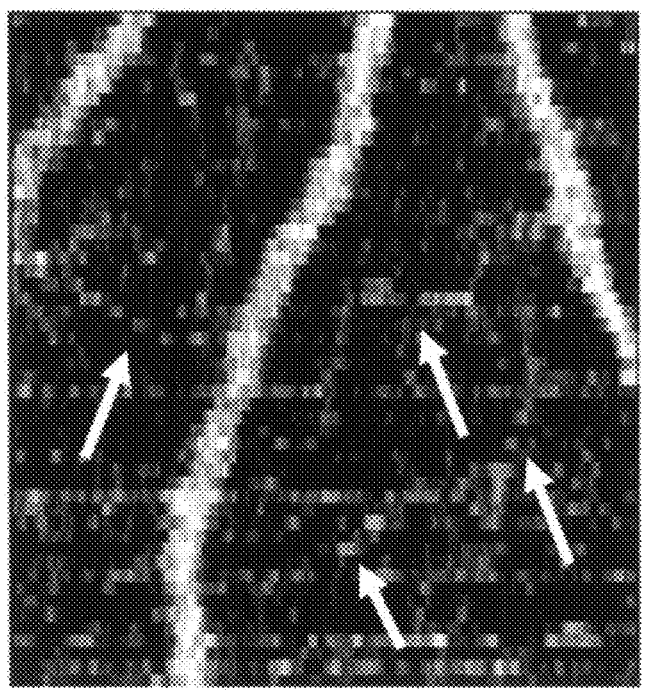
FIG. 35A shows a BM-scan en face summation image of intensity and FIG. 35B shows BM-scan en face summation image of phase variance contrast.
Figure 35A:
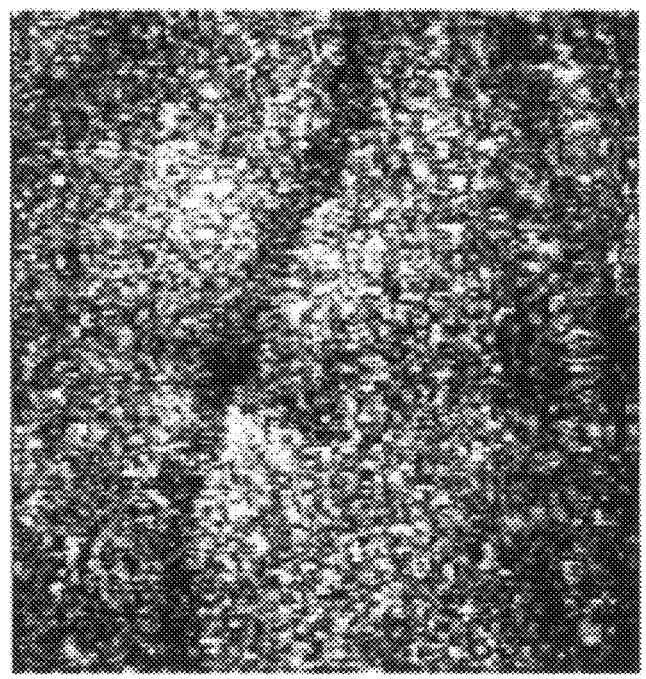
Figure 37B:
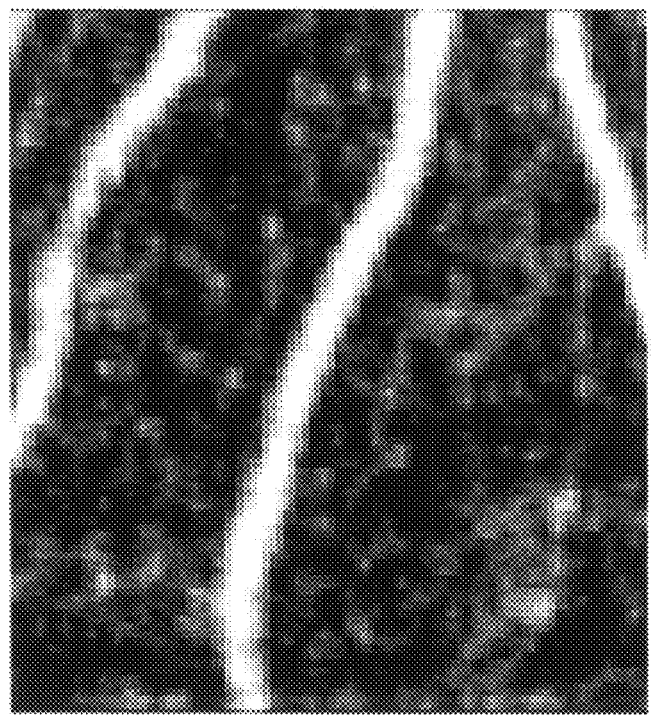
FIGS. 37A and B display the mean contrast summation images from two different acquisitions of the repeating BM-scan method, summed over the top half of the retina. Images in FIGS. 37A and B were acquired with perpendicular primary transverse scan directions. Images were extrapolated to the size of 100×100 pixel for comparison.
Figure 37A:
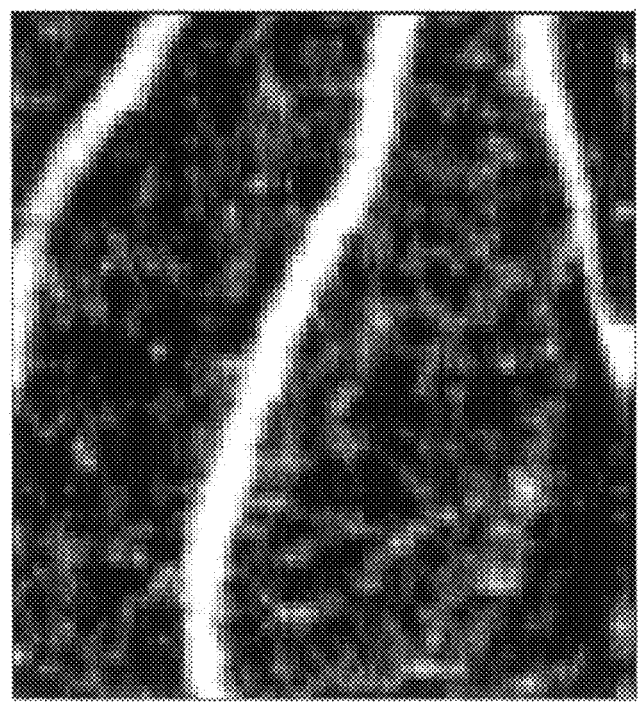

While the description above refers to particular techniques for performing the inventive method, it should be readily apparent to people of ordinary skill in the art that a number of modifications may be made without departing from the spirit thereof. The presently disclosed embodiments are, therefore, to be considered in all respects as illustrative and not restrictive.

REFERENCES

[1] B. Hyle Park, Mark C. Pierce, Barry Cense, Seok-Hyun Yun, Mircea Mujat, Guillermo J. Tearney, Brett E. Bouma, Johannes F. de Boer, "Real-time fiber-based multi-functional spectral domain optical coherence tomography at 1.3 µm," Opt. Express Vol. 13, No. 11, 3931-3944 (2005)

What is claimed:
1. A method to ascertain motion contrast in a sample in an optical coherence tomography system comprising;
    acquiring data using the optical coherence tomography system by performing multiple B-scans of the sample, wherein each of said B-scans comprises data acquired during multiple scans over a range of transverse locations;

ascertaining phase variance of the data, wherein said phase variance is ascertained based on data of said B-scans; and ascertaining the motion contrast in the sample based upon the phase variance.

2. The method of claim 1, wherein the step of ascertaining phase variance of the data comprises:

using the temporal evolution of the measured phase variance of the motion in the sample to identify and characterize mobile scatterers within the images obtained from one or more scans of the sample.

3. The method of claim 1, wherein the method further comprises:

ascertaining the temporal fluctuations in intensity of the data acquired using the optical coherence tomography system and ascertaining the motion contrast based upon the temporal fluctuation.

4. The method of claim 1, wherein the method further comprises:

estimating refractive index variations within flow regions and ascertaining the motion contrast based upon the estimate.

5. The method of claim 4, wherein estimating refractive index variations comprises time separation of the onset of refractive index shadowing within one or more phase contrast image and the refractive indices of the constituents within the flow region.

6. The method of claim 1, wherein the multiple B-scans comprise a MB-scan, a BM-scan, or both.

7. The method of claim 1, wherein the optical coherence tomography system comprises a Fourier domain optical coherence tomography system.

8. The method of claim 7, wherein the Fourier domain optical coherence tomography system comprises spectral domain optical coherence tomography, swept source optical coherence tomography, or optical frequency domain imaging.

9. A method of ascertaining regions of different mobility in a sample comprising:

ascertaining motion contrast according to the method of claim 1 in a plurality of regions; and identifying one or more regions of mobility within said sample.

10. The method of claim 9, wherein said one or more regions of mobility identified are three-dimensional.

11. The method of claim 10, wherein said one or more three-dimensional regions of mobility identified comprise a three-dimensional vasculature, a vessel of interest, or combination thereof.

12. A method of diagnosing and treating disease in a patient in need thereof comprising:

ascertaining motion contrast according to the method of claim 1 in an area of the patient in need thereof, determining blood flow in the area based upon the motion contrast, and diagnosing the patient based upon the blood flow.

13. The method of claim 1, further comprising:

estimating transverse flow velocity based upon the motion contrast.

14. The method of claim 1, wherein said phase variance is ascertained independent of intensity data.

15. The method of claim 1, wherein said phase variance is ascertained for a given depth $z_i$ for a time separation T, based on a combination of factors affecting measurement, wherein the factors comprise scatterer motion, bulk motion, signal-to-noise ratio (SNR), or other error factors.

16. The method of claim 1, wherein said phase variance is due to transverse motion and ascertained according to:

$$\sigma_{\Delta\phi}^2 = \frac{4\pi}{3}\left(1 - \exp\left(-2\left(\frac{\Delta x}{d}\right)^2\right)\right) = \frac{4\pi}{3}\left(1 - \exp\left(-2\left(\frac{v_X T}{d}\right)^2\right)\right),$$

wherein $\sigma_{\Delta\phi}^2$ denotes phase variance; $\Delta x$ denotes transverse motion of the scatterer between phase measurements; $v_x$ denotes transverse velocity during the time separation T; and d denotes beam width.

17. A computer readable medium having computer executable instructions for ascertaining motion contrast in a sample in an optical coherence tomography system comprising:

acquiring data using the optical coherence tomography system by performing multiple B-scans of the sample, wherein one of said one or more scans comprises data acquired during multiple scans over a range of transverse locations;

ascertaining phase variance of the data, wherein said phase variance is ascertained based on data of said B-scans; and ascertaining the motion contrast in the sample based upon the phase variance.

18. An optical coherence tomography system comprising:

a computer readable medium having computer executable instructions for ascertaining motion contrast in a sample comprising:

acquiring data using the optical coherence tomography system by performing multiple B-scans of the sample, wherein one of said one or more scans comprises data acquired during multiple scans over a range of transverse locations; ascertaining phase variance of the data, wherein said phase variance is ascertained based on data of said B-scans; and ascertaining the motion contrast in the sample based upon the phase variance.

19. A method to ascertain motion contrast in a sample in an optical coherence tomography system comprising:

acquiring data using the optical coherence tomography system by performing one or more scans of the sample;

ascertaining phase variance of the data, wherein said phase variance is ascertained independent of intensity data; and ascertaining the motion contrast in the sample based upon the phase variance.

20. The method of claim 19, wherein said one or more scans comprise multiple B-scans.

* * * * *